(12) United States Patent
Flint et al.

(10) Patent No.: US 12,397,176 B2
(45) Date of Patent: Aug. 26, 2025

(54) METHOD FOR USE WITH A RADIOTHERAPY DEVICE

(71) Applicant: Elekta Limited, Crawley (GB)

(72) Inventors: Chris Flint, Crawley (GB); Keith Richardson, Crawley (GB); Marcelo Jordao, Crawley (GB); Alessandra Chiap, Crawley (GB); Mark Holmes, Crawley (GB)

(73) Assignee: Elekta Limited, Crawley (GB)

( * ) Notice: Subject to any disclaimer, the term of this patent is extended or adjusted under 35 U.S.C. 154(b) by 890 days.

(21) Appl. No.: 17/309,048

(22) PCT Filed: Oct. 14, 2019

(86) PCT No.: PCT/GB2019/052919
§ 371 (c)(1),
(2) Date: Apr. 16, 2021

(87) PCT Pub. No.: WO2020/079409
PCT Pub. Date: Apr. 23, 2020

(65) Prior Publication Data
US 2021/0370098 A1    Dec. 2, 2021

(30) Foreign Application Priority Data
Oct. 18, 2018 (GB) .................................. 1817013

(51) Int. Cl.
*A61N 5/10* (2006.01)
*G01R 19/165* (2006.01)
(Continued)

(52) U.S. Cl.
CPC ..... *A61N 5/1075* (2013.01); *G01R 19/16571* (2013.01); *G16H 40/40* (2018.01);
(Continued)

(58) Field of Classification Search
CPC .......... A61N 5/1075; A61N 2005/1089; G01R 19/16571; G16H 40/40; H01J 3/028;
(Continued)

(56) References Cited

U.S. PATENT DOCUMENTS 6,424,159 B1 * 7/2002 Jansen ..................... A61B 6/56
324/513
6,426,997 B1 * 7/2002 Fuchs ...................... H05G 1/34
378/118
(Continued)

FOREIGN PATENT DOCUMENTS

DE    10011294 A1    10/2000
GB    1203944 A    9/1970
(Continued)

OTHER PUBLICATIONS

"Chinese Application Serial No. 201980084013.2, Office Action dated Dec. 26, 2023", w English Translation, (Dec. 26, 2023), 12 pgs.
(Continued)

*Primary Examiner* — Catherine T. Rastovski
*Assistant Examiner* — Brian Butler Geiss
(74) *Attorney, Agent, or Firm* — Schwegman Lundberg & Woessner, P.A.

(57) ABSTRACT

Described is a method of determining whether repair or replacement of an electron gun of a radiotherapy device should be scheduled. The radiotherapy device comprises a linear accelerator and is configured to provide therapeutic radiation to a patient. The radiotherapy device comprises a vacuum tube comprising the electron gun, a waveguide configured to accelerate electrons emitted by the electron gun toward a target to produce said radiation. The radiotherapy device comprises also comprises a current sensor, the current sensor being configured to provide signals
(Continued)

indicative of current supplied to the electron gun. The method comprises receiving a current value, processing the current value, and based on the processing of the current value, determining whether repair or replacement of the electron gun should be scheduled. Processing the current value comprises determining whether the current value meets at least one threshold criterion, and determining whether the current value has changed by at least a threshold amount in a particular time period.

13 Claims, 12 Drawing Sheets

(51) Int. Cl.
    *G16H 40/40*    (2018.01)
    *H01J 3/02*    (2006.01)
    *H05H 9/04*    (2006.01)

(52) U.S. Cl.
    CPC ...... *H01J 3/028* (2013.01); *A61N 2005/1089* (2013.01); *H05H 9/048* (2013.01)

(58) Field of Classification Search
    CPC .. H01J 3/02; H05H 9/048; H05G 1/54; G06Q 10/0631
    See application file for complete search history.

(56) References Cited

U.S. PATENT DOCUMENTS

| | | |
|---|---|---|
| 2003/0058992 A1 | 3/2003 | Marziale et al. |
| 2004/0138920 A1 | 7/2004 | Sawanaga et al. |
| 2005/0157849 A1* | 7/2005 | Radley .................. A61B 6/586 378/207 |
| 2012/0229024 A1 | 9/2012 | Large |
| 2013/0315378 A1 | 11/2013 | Yabugami |
| 2014/0266713 A1 | 9/2014 | Sehgal et al. |
| 2018/0133518 A1* | 5/2018 | Harper ................ A61N 5/1049 |

FOREIGN PATENT DOCUMENTS

| | | |
|---|---|---|
| JP | 2003150101 A | 5/2003 |
| JP | 2012247379 A | 12/2012 |

OTHER PUBLICATIONS

"European Application Serial No. 19790757.9, Office Action dated Mar. 13, 2023", (Mar. 13, 2023), 8 pgs.

"International Application Serial No. PCT/GB2019/052919, International Search Report mailed Dec. 2, 2019", (Dec. 2, 2019), 4 pgs.

"International Application Serial No. PCT/GB2019/052919, Written Opinion mailed Dec. 2, 2019", (Dec. 2, 2019), 7 pgs.

"United Kingdom Application Serial No. 1817013.4, Office Action mailed Apr. 17, 2019", (Apr. 17, 2019), 5 pgs.

Albano, Michele, et al., "Sensors: the enablers for proactive maintenance in the real world", 2018 5th International Conference on Control, Decision and Information Technologies (CoDIT). IEEE, (2018), pp. 569-574.

Susto, Gian Antonio, et al., "A predictive maintenance system based on regularization methods for ion-implantation", 2012 SEMI Advanced Semiconductor Manufacturing Conference. IEEE, (2012), pp. 175-180.

* cited by examiner

METHOD FOR USE WITH A RADIOTHERAPY DEVICE

PRIORITY APPLICATIONS

This application is a U.S. National Stage Filing under 35 U.S.C. § 371 from International Application No. PCT/GB2019/052919, filed on Oct. 14, 2019, and published as WO2020/079409 on Apr. 23, 2020, which claims the benefit of priority to United Kingdom Application No. 1817013.4, filed on Oct. 18, 2018; the benefit of priority of each of which is hereby claimed herein, and which applications and publication are hereby incorporated herein by reference in their entirety.

This disclosure relates to the fields of predictive maintenance and remote diagnostics, and in particular to methods of determining whether to schedule repair or replacement of an electron gun in a radiotherapy device, determining the nature of a fault in a radiotherapy device and determining whether maintenance of a radiotherapy device should be scheduled.

BACKGROUND

Radiotherapy devices are an important tool in modern cancer treatment. Radiotherapy devices are large, complex machines, with many moving parts and inter-operating mechanisms. Despite precision engineering and rigorous testing, some component parts of a radiotherapy device may start to degrade over its lifetime. This can sometimes lead to sub-optimal operation and even the occasional safety override.

If at any point during treatment a radiotherapy device starts to function outside of its normal operating parameters, a safety override or "interrupt" occurs, whereby the machine stops delivering radiation to ensure patient safety. Such an event is inconvenient, as it adds time to the treatment, and in some cases means the treatment session must finish prematurely. Unplanned equipment downtime can disrupt planned treatment schedules, and may be expensive for the owner, be it due to loss of revenue, servicing and repair costs, or both.

It has been surmised that predictive maintenance and/or remote diagnostic techniques could be applied to radiotherapy machines. However, given the complexity of the machines and the sheer volume of data which may be gathered during operation, it is difficult to know how to analyse any available data to inform the predictive maintenance techniques. For example, while particular data patterns may be indicative of a particular fault or indicative that a particular component has degraded to a degree that it will shortly begin operation outside of its optimal operating parameters, identifying the link between particular data patterns and the particular fault or degrading component is often non-intuitive even for experienced service engineers. Even when a problematic machine is identified, trying to ascertain the nature of the fault is very difficult given the abundance of data and the complex interrelationships between the various components of the machine. In other words, even if a wealth of data from a radiotherapy device is available, remotely determining the nature of a fault or assessing the condition of a particular component is not a trivial matter.

The present disclosure relates, in part, to identifying that an electron gun of a radiotherapy device is nearing the time at which it should be replaced or repaired. To date, no such predictive approach has been possible, and existing methods of servicing and repair involve noting that a particular device has undergone multiple safety overrides, and sending a field service engineer to inspect the machine and diagnose and fix the problem. Often, the type of problem or the component which is at fault is not known in advance, and hence time consuming diagnostic testing must be performed on-site. Existing methods therefore result in a significant amount of machine down time. Also, in existing methods, a field service engineer is not made aware of a potential issue until the component has degraded to a point where the radiotherapy machine is undergoing safety interrupts, or even until the point where the radiotherapy machine cannot operate within its safety parameters. This means that the servicing of the radiotherapy machine is often scheduled at a time which is inconvenient, or inefficient in terms of both field service engineer resources and the resources of the hospital or other machine owner.

The present invention seeks to address these and other disadvantages encountered in the prior art by providing methods of determining, preferably remotely, whether repair or replacement of an electron gun in a radiotherapy device should be scheduled, determining the nature of a fault in a radiotherapy device and determining whether maintenance of a radiotherapy device should be scheduled.

SUMMARY

An invention is set out in the independent claims Optional features are set out in the dependent claims.

According to an aspect of the invention there is provided a method of determining whether repair or replacement of an electron gun of a radiotherapy device should be scheduled. The radiotherapy device comprising a linear accelerator. The device is configured to provide therapeutic radiation to a patient, and comprises a vacuum tube comprising the electron gun, a waveguide configured to accelerate electrons emitted by the electron gun toward a target to produce said radiation; and a current sensor. The current sensor is configured to provide signals indicative of current supplied to the electron gun. The method comprises receiving a current value, processing the current value and, based on the processing of the current value, determining whether repair or replacement of the electron gun should be scheduled. The processing of the current value comprises determining whether the current value meets at least one threshold criterion, and determining whether the current value has changed by at least a threshold amount in a particular time period.

According to a further aspect of the invention there is provided a method of determining whether maintenance of a radiotherapy device should be scheduled, the radiotherapy device comprising a linear accelerator and being configured to provide therapeutic radiation to a patient, the radiotherapy device comprising: a vacuum tube comprising: an electron gun; a waveguide configured to accelerate electrons emitted by the electron gun toward a target to produce said radiation; and a current sensor, the current sensor being configured to provide signals indicative of current supplied to the electron gun; the method comprising: receiving a current value derived from signals provided by the current sensor; processing the current value to determine whether the current value meets at least a first threshold criterion; determining whether a total amount of time the electron gun has been in a radiation mode meets at least a second threshold criterion; and if the first threshold criterion and the second threshold criterion are met, determining whether maintenance of the radiotherapy device should be scheduled.

According to a further aspect of the invention there is provided a method of determining the nature of a fault in a radiotherapy device, the radiotherapy device comprising a linear accelerator and being configured to provide therapeutic radiation to a patient, the radiotherapy device comprising: a gantry configured to rotate the vacuum tube around a patient such that radiation can be directed toward the patient from multiple angles and/or directions around the patient; a vacuum tube comprising: an electron gun; a waveguide configured to accelerate electrons emitted by the electron gun toward a target to produce said radiation; and a voltage sensor, configured to provide signals indicative of voltage applied to the electron gun, the method comprising: receiving voltage values derived from signals provided by the voltage sensor during a rotation of the gantry; processing the voltage values, wherein processing the voltage values comprises determining whether the voltage values meet at least one first threshold criterion; and based on the processing of the voltage values, determining whether the nature of the fault is associated with the electron gun.

FIGURES

Specific embodiments are now described, by way of example only, with reference to the drawings, in which.

Figure 8A:
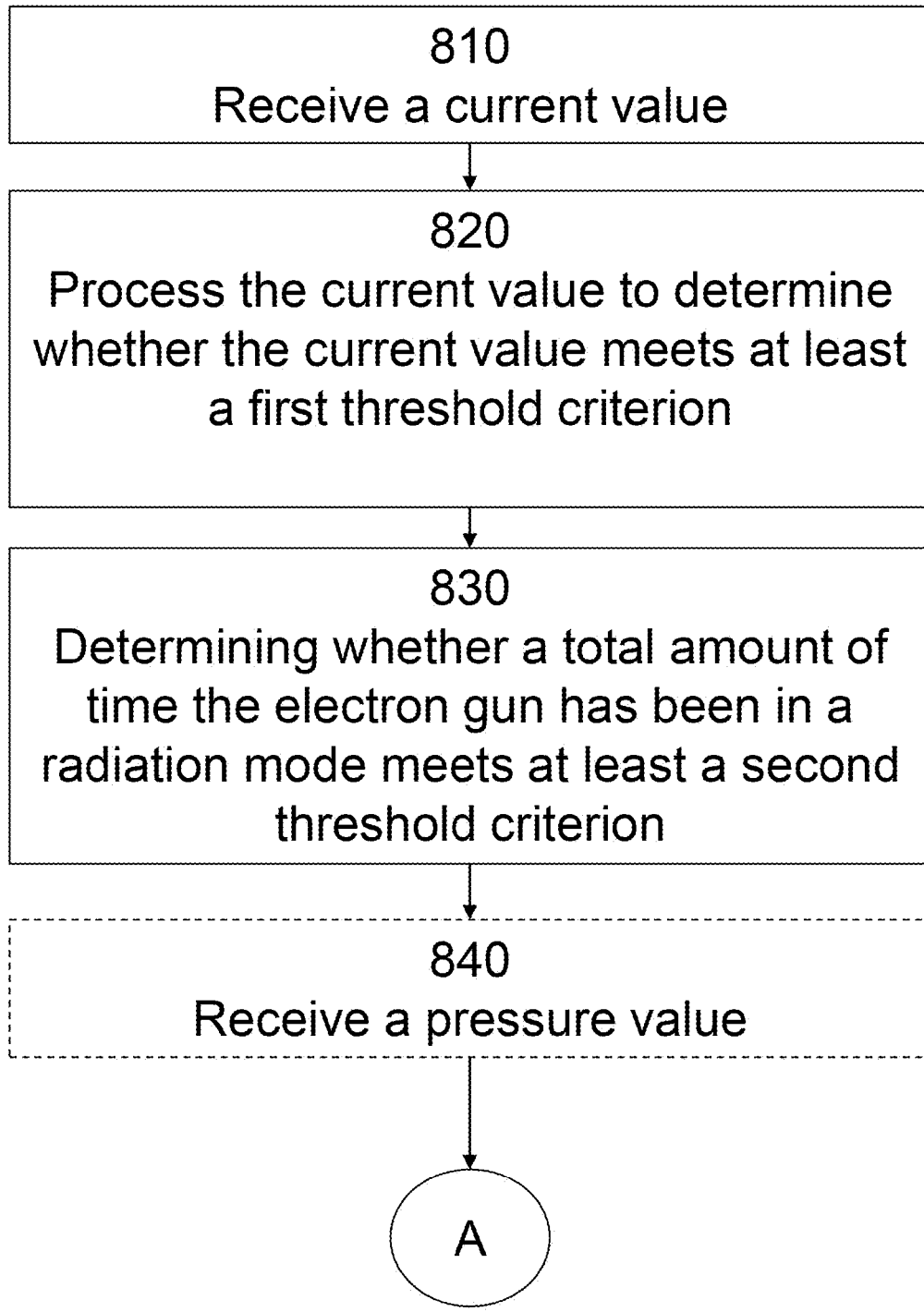
Figure 8B:
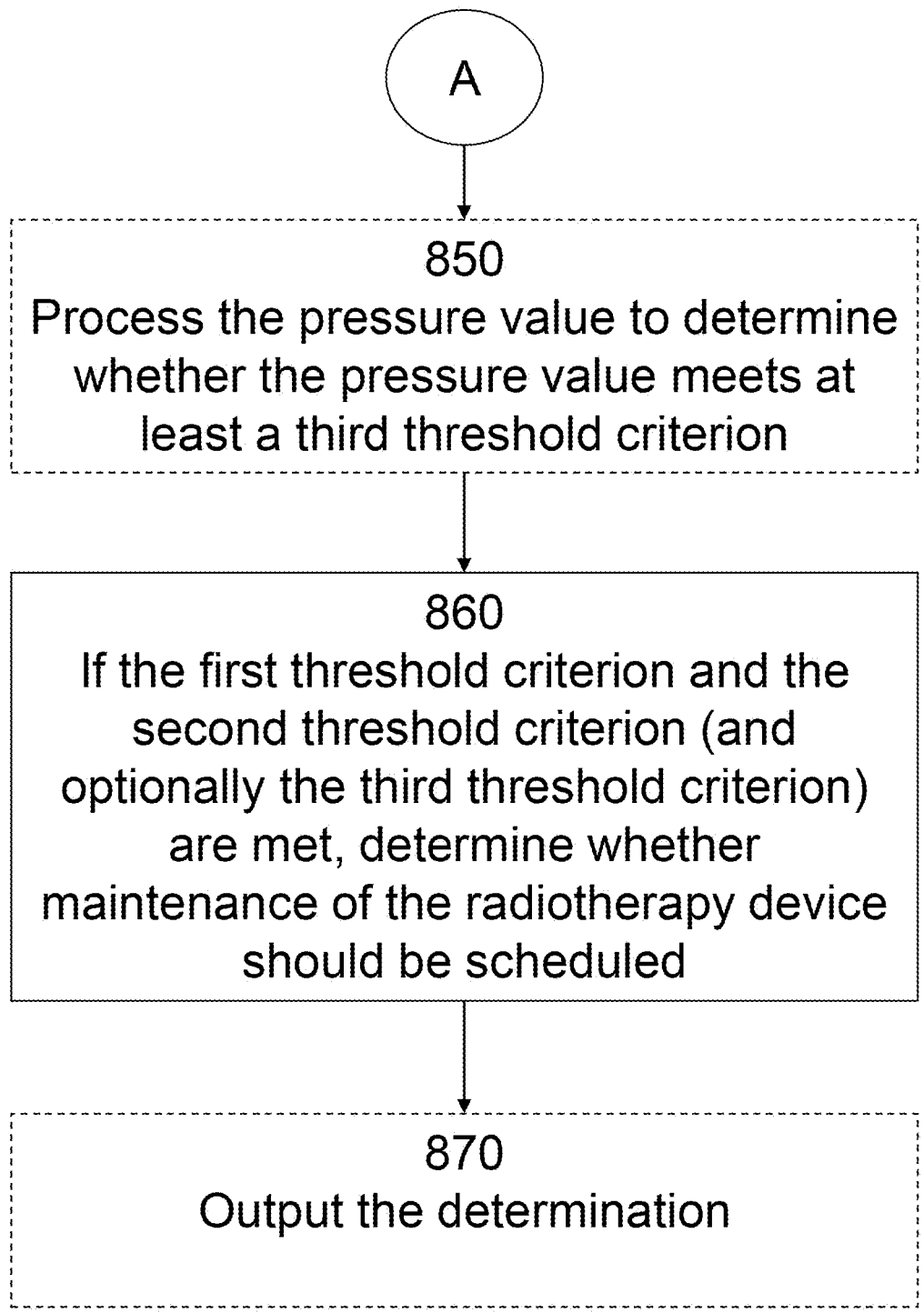
Figure 9A:
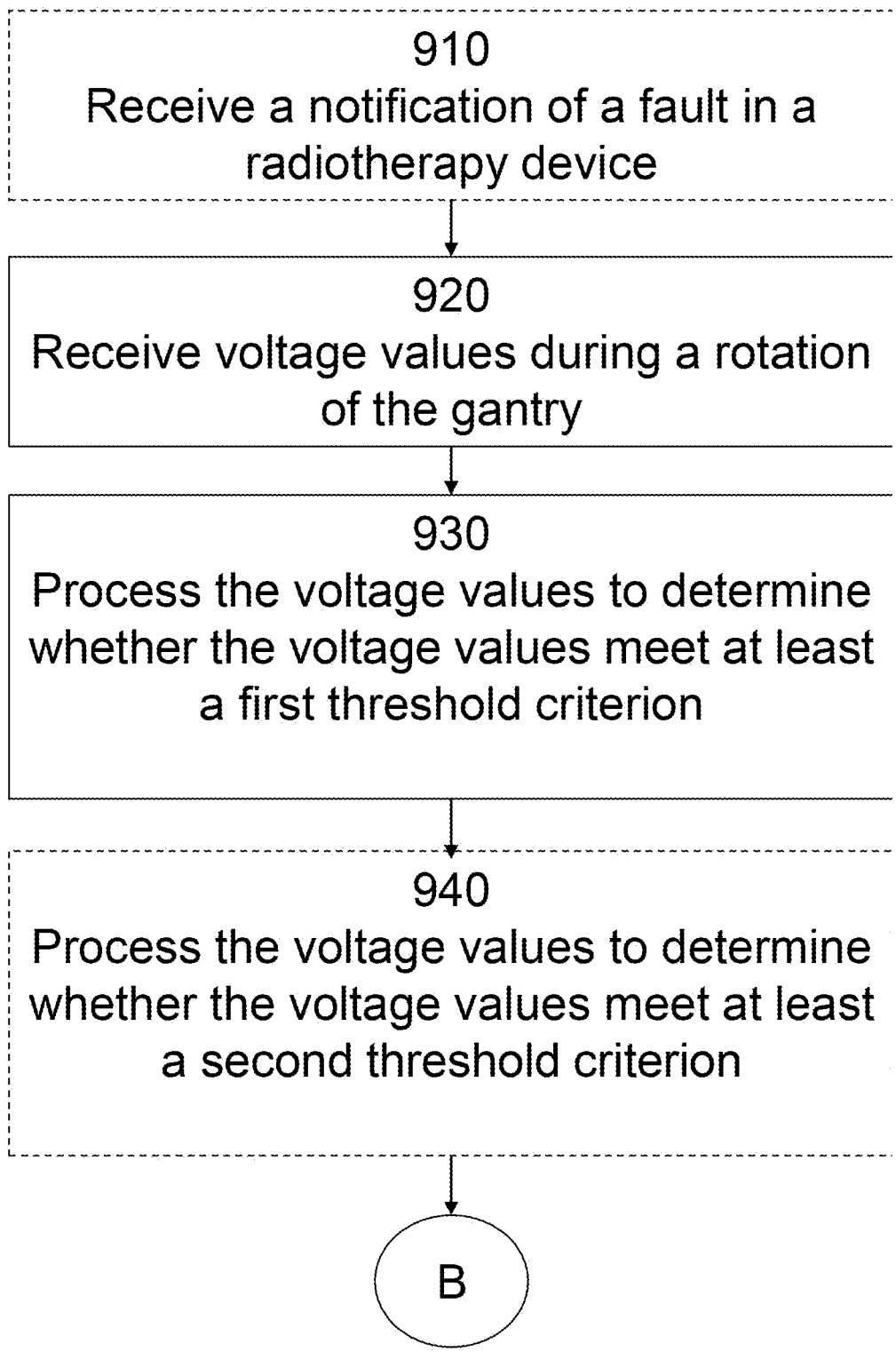
Figure 9B:
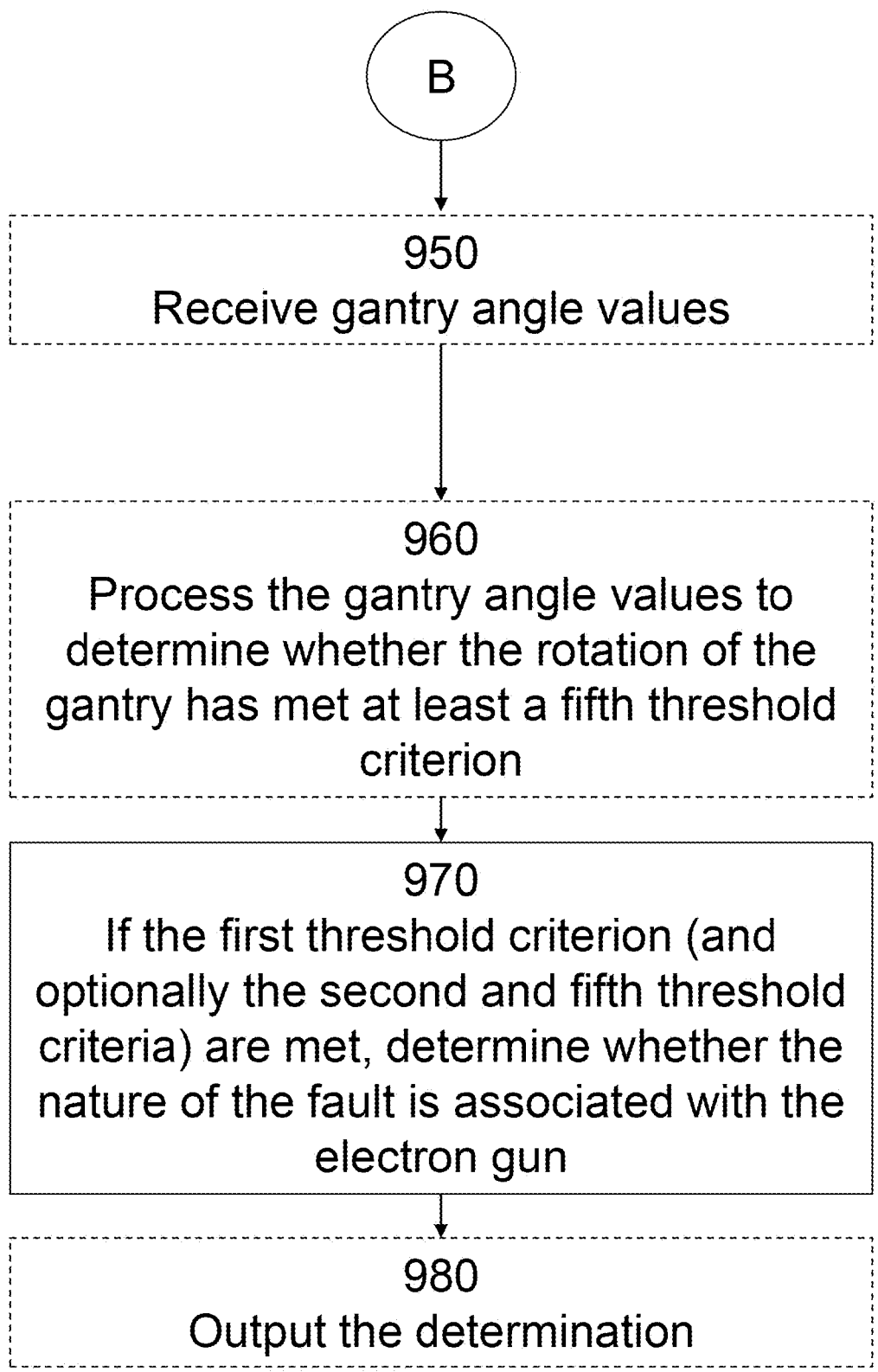
Figure 10:
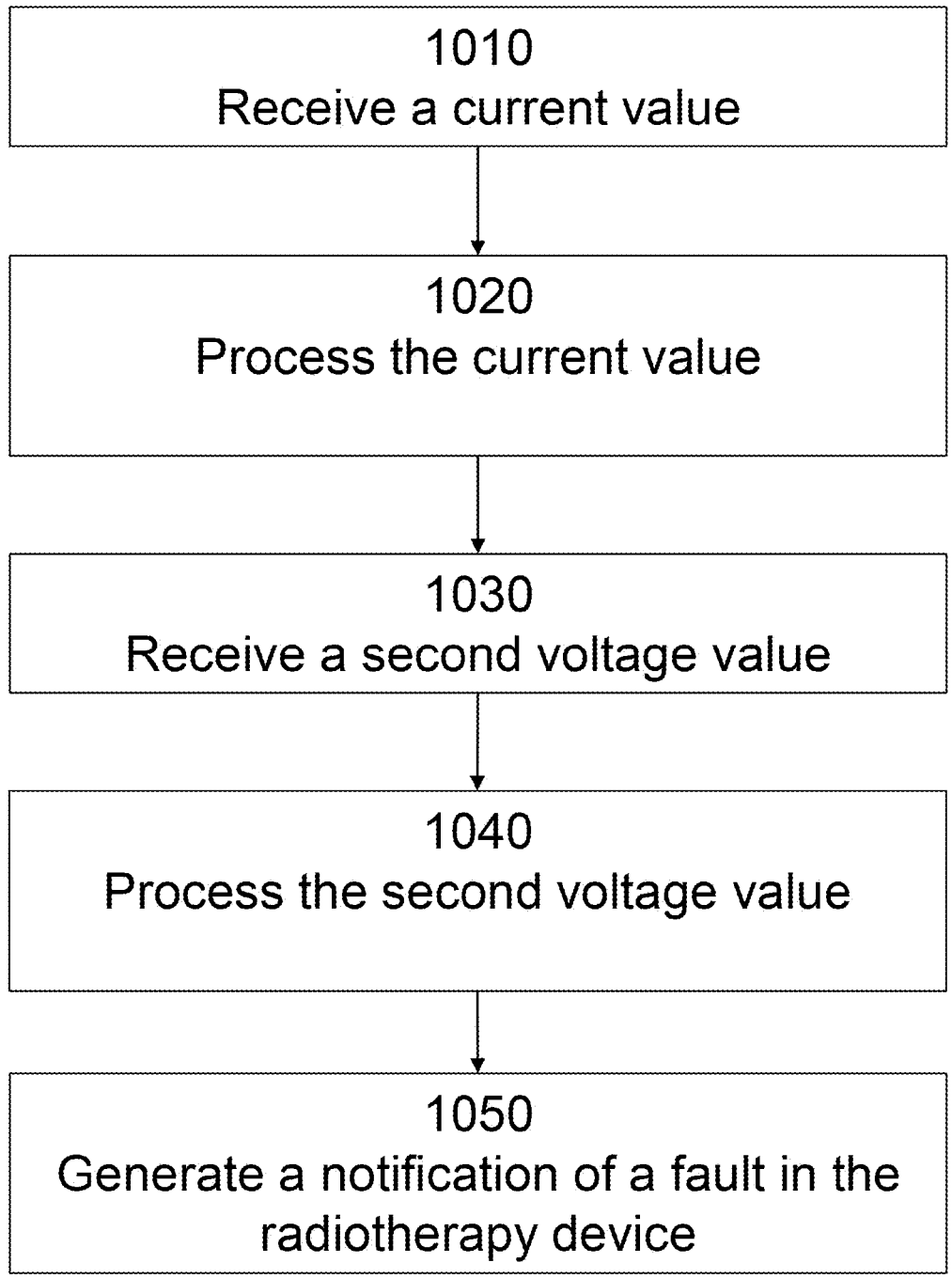

FIGS. 8*a* and 8*b* are a flowchart which depicts a method according to the present disclosure;

FIGS. 9*a* and 9*b* are a flowchart which depicts a method according to the present disclosure; and FIG. 10 is a flowchart which depicts a method according to the present disclosure.

DETAILED DESCRIPTION

The present disclosure relates to a method determining whether a component or components of a radiotherapy machine or device should be serviced or replaced, and/or to determining to what degree such a component is operating within safety parameters and optimal operational parameters. The radiotherapy device may be suitable for delivering a beam of radiation to a patient in order to treat a tumour. An example of a radiation source for producing a therapeutic beam of radiation is a linear accelerator (LINAC). Clinical LINAC devices are configured to deliver high energy radiation to a patient.

Radiotherapy machines are beginning to be configured to produce and record a large amount of data as they operate; for example, radiotherapy machines are configured to provide sensor readings from a variety of different sensors. These sensors produce data which can be stored in a database. Radiotherapy devices may also be configured to allow remote connection, enabling service engineers to access a wealth of information about any connected machine without having to travel to the site where the machine is located. It is expected that, in many cases, machines may be returned to optimal performance without an engineer ever having to physically interact with the machine. However, there will still be occasions where the fault cannot be fixed remotely, and an engineer must be sent to: inspect the machine; determine the nature of the fault; and perform any maintenance required. If the repair involves replacing a part, further machine downtime is required before the machine can be brought back online.

Some of the present methods involve evaluating the condition and/or performance of a component of radiotherapy equipment during its operation in order to identify and determine, preferably remotely, whether the component is nearing the end of its operational life and thus whether the component should be replaced or repaired. Others of the present methods involve determining the nature of a fault in a radiotherapy device or determining whether maintenance of a radiotherapy device should be scheduled. The present application relates, in part, to determining whether a filament of a cathode of an electron gun is approaching the end of its operational life. Such techniques are advantageous as they allow a manufacturer or maintenance service provider to attend the machine knowing what will be required to fix the machine prior to arrival. Some of the disclosed techniques allow the operation of the electron gun to be monitored, and hence electron gun cathode filaments which are approaching the end of their operational life but which are still operating within required safety parameters can be identified. This in turn allows, for example, repair and/or replacement of the electron gun to be scheduled for the next convenient service point. The disclosed methods help to reduce machine downtime and thereby minimise disruption to the machine's normal operation. The disclosed techniques can also be used to more effectively plan machine downtime for times which are more convenient or cost-effective for the owner of the equipment and/or the patients.

As outlined above, the present application relates, in part, to determining the nature of a fault in a radiotherapy device, in particular, to determine whether there is a fault with the electron gun. For example, some of the present methods involve determining that the electron gun of a radiotherapy device has come loose from its carrier or, more particularly, that the cathode of the electrode gun has come loose from its carrier. This can cause the radiotherapy device to operate sub-optimally Such techniques are advantageous as they allow a manufacturer or maintenance service provider to attend the machine knowing what will be required to fix the machine prior to arrival. The disclosed techniques can help to reduce machine downtime and thereby minimise disruption to the machine's normal operation. The disclosed techniques can also be used to more effectively plan machine downtime for times which are more convenient or cost-effective for the owner of the equipment and/or the patients.

As outlined above, the present application relates, in part, to determining whether maintenance of a radiotherapy device should be scheduled, in particular, as a result of issues with the quality of the vacuum in a vacuum tube of the radiotherapy device. The operating life time of an electron gun, know and a gun life, can be negatively affected by a poor vacuum quality in the vacuum tube. As such, identifying such vacuum quality issues and scheduling maintenance of a radiotherapy device to address the vacuum quality issues can extend the gun life of the electron gun of the radiotherapy device. Typically, vacuum quality issues are introduced during an electron gun replacement. For example, a vacuum leak or contamination could be introduced during the process of replacing an electron gun.

As is known to the skilled person, a LINAC comprises an electron gun, which operates to inject electrons into a waveguide in a manner described further below. The electron gun comprises a cathode which is suitable for emitting, and configured to emit, electrons via the process of thermionic emission. The cathode comprises a filament which is either made of, coated with, or which otherwise comprises a suitable emissive material.

Current is passed through the cathode filament in order to heat it up, and the emissive material emits electrons into the vacuum tube which are then accelerated in the waveguide toward a target. Suitable cathode coatings include barium oxide, strontium oxide and calcium oxide. By way of another example, the filament may be a thoriated tungsten filament, In such arrangements, a small amount of thorium is added to the tungsten material which comprises the filament.

However, the cathode filament used in electron guns has only a limited operational life time. This is because the emissive layers on coated cathodes degrade slowly with time. As the filament or filament coating degrades, fewer electrons are emitted as the filament is heated. Also, while the electron gun typically sits in a vacuum tube in an UHV environment, the cathode filament still contacts a small amount of gas molecules. These gas molecules can be absorbed into the cathode's coating, causing further degradation of the cathode filament material. This results in reduced emissivity, which is exacerbated if any small leaks are present in the vacuum tube.

An electron gun life time, or "gun life" is the total amount of time an electron gun can operate in a radiation mode, in which electrons are being emitted by the electron gun, before the rate at which electrons are emitted drops below an acceptable rate. An expected gun life is simply an expected amount of time an electron gun can operate in a radiation mode before the rate at which electrons are emitted drops below an acceptable rate. An example expected gun life is 1,000 hours of operation in a radiation mode.

A radiation mode or active mode is mode in which the electron gun is emitting electrons. Conversely, a standby mode or inactive mode is where the electron gun is not emitting electrons.

High-Level Overview of a LINAC

Figure 1:
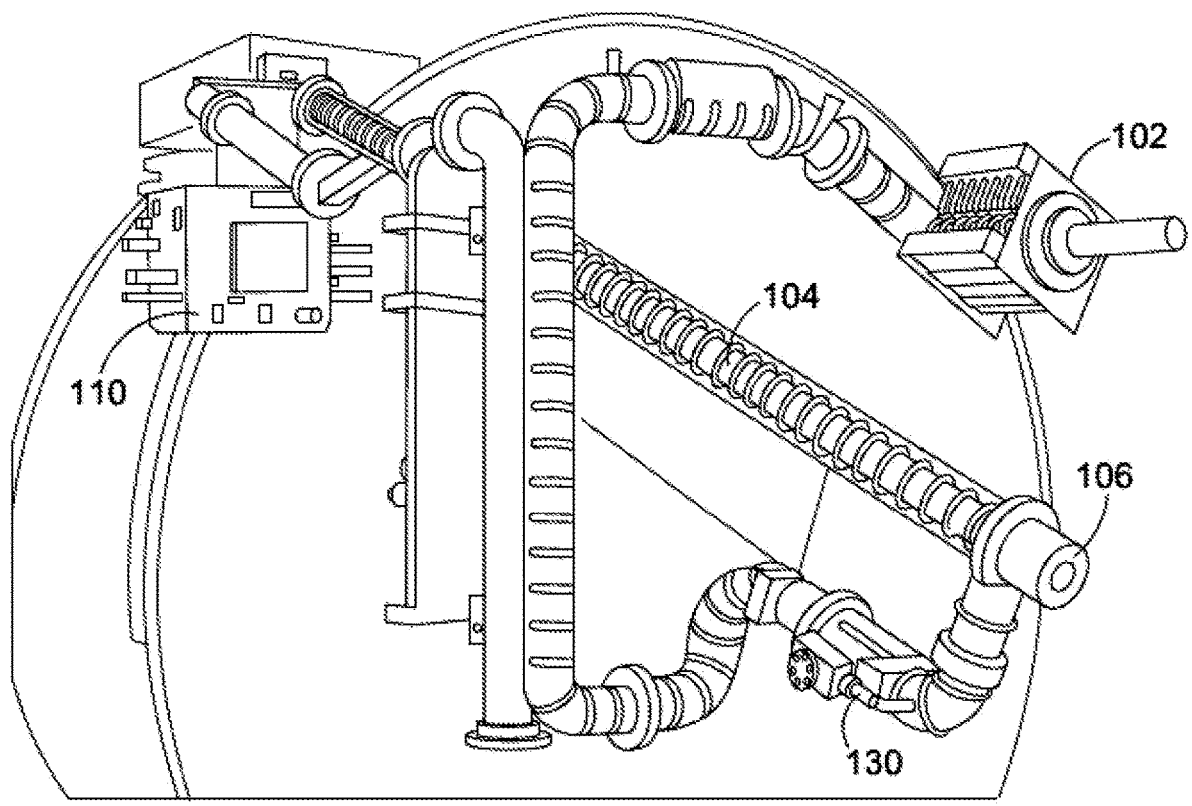
FIG. 1 depicts a schematic illustration of a radiotherapy device comprising a LINAC.

FIG. 1 depicts a LINAC suitable for delivering, and configured to deliver, a beam of radiation to a patient during radiotherapy treatment. In operation, the LINAC device produces and shapes a beam of radiation and directs it toward a target region within the patient's body in accordance with a radiotherapy treatment plan.

A medical LINAC machine is by necessity complex, with many inter-operating component parts. A brief summary of the operation of a typical LINAC will be given with respect to the LINAC device depicted in FIG. 1, which comprises a source of radiofrequency waves, a waveguide, a source of electrons, a system capable of creating a strong vacuum comprising one or more vacuum pumps 130, a heavy metal target which produces X-rays when hit by an electron beam, and a complex arrangement of magnets capable of re-directing and focusing the electron beam onto the target. The device depicted in FIG. 1 also comprises a treatment head which houses various apparatus configured to, for example, collimate and shape the resultant X-ray beam.

The source 102 of radiofrequency waves, such as a magnetron, produces radiofrequency waves. The source 102 of radiofrequency waves is coupled to the waveguide 104, and is configured to pulse radiofrequency waves into the waveguide 104. Radiofrequency waves pass from the source 102 of radiofrequency waves through an RF input window and into a RF input connecting pipe or tube. The RF input connecting pipe or tube is coupled with the waveguide, and may join the waveguide at a substantially 90° angle as shown in FIG. 1. The connecting tube or pipe may join the waveguide via a so-called 'elbow joint' or 't-shaped joint'. A source 106 of electrons, such as an electron gun, is coupled to the waveguide 104 and is configured to inject electrons into the waveguide 104. In the source 106 of electrons, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source 106 and the waveguide 104 is such that the radiofrequency waves accelerate the electrons to very high energies as they propagate through the waveguide 104.

The design of the waveguide 104 depends on whether the LINAC accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they pass into a flight tube. The flight tube may be connected to the waveguide by a connecting tube. This connecting tube or connecting structure may be called a drift tube. The drift tube also forms part of the vacuum tube. RF waves exit the waveguide via an RF output connecting pipe or tube coupled with the drift tube. As with the RF input pipe which introduces RF to the waveguide, the pipe or tube through which RF exits the waveguide connects to the vacuum tube via an elbow joint or 'T-shaped' joint. RF passes out from the vacuum system via an RF output window which seals the vacuum system.

The flight tube is kept under vacuum conditions by the pump system. The electrons travel along a slalom path toward the heavy metal target. The target may comprise, for example, tungsten. Whilst the electrons travel through the flight tube, an arrangement of focusing magnets act to direct and focus the beam on the target. The slalom path allows the overall length of the LINAC to be reduced while ensuring that the beam of accelerated electrons, which is comprised of electrons with a small spread of energies, is focused on the target.

To ensure that propagation of the electrons is not impeded as the electron beam travels toward the target, the waveguide 104 is evacuated using a vacuum system comprising a vacuum pump 130 or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104. Together, the electron gun 106, waveguide 104 and the flight tube form a vacuum tube in which electrons can be accelerated and directed toward a target in vacuum conditions. In implementations comprising a drift tube connecting the waveguide 104 to the flight tube, the drift tube also forms part of the vacuum tube. The vacuum tube has two ends. The ends may be described as opposing ends. The electron gun 106 is located at a first end of the vacuum tube and the flight tube is located at a second end of the vacuum tube. In other words, the flight tube is located at a distal end of the waveguide 104, and hence vacuum tube, from the electron gun 106.

The combination of the components kept under vacuum, e.g. the vacuum tube and any connecting pipes and tubes, for example those connecting tubes and pipes which couple the RF input and output windows to the vacuum tube and the internal volume of the pumps, may be referred to as the vacuum system. The vacuum system is sealed and is constantly kept under vacuum. To produce the necessary high vacuum conditions, the vacuum system may undergo several stages of pumping before the high quality vacuum may be maintained using e.g. ion pumps. For example, first, a normal piston-based pump may be used, followed by a stage wherein the pressure inside the vacuum system is further lowered using a turbo-molecular pump. Finally, ion pumps are used to ensure the system is kept at ultra-low pressure.

When the high energy electrons hit the target, X-rays are produced in a variety of directions. The target is located inside the flight tube, and is located at the end of the flight tube to seal the vacuum system. The flight tube also comprises a target window, which is transparent to X-rays, which his positioned to allow the X-rays which are produced when the LINAC is in operation to pass from the evacuated flight tube through the target window and into the treatment head 110. At this point, a primary collimator blocks X-rays travelling in certain directions and passes only forward travelling X-rays to produce a cone shaped beam. The X-rays are filtered, and then pass through one or more ion chambers for dose measuring. The beam can be shaped in various ways by beam-shaping apparatus, for example by using a multi-leaf collimator, before it passes into the patient as part of radiotherapy treatment.

In some implementations, the LINAC is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the LINAC. In essence, it is possible to swap between the first and second mode by moving the heavy metal target in or out of the electron beam path and replacing it with a so-called 'electron window'. The electron window is substantially transparent to electrons and allows electrons to exit the flight tube.

The end of the flight tube may be sealed by a component which comprises both a target and an electron window. It is then possible to swap between the first and second mode by moving the flight tube such that the electron beam points toward either the target or the electron window. The drift tube, which connects the waveguide to the start of the flight tube, is therefore slightly flexible to allow the flight tube to move. In other words, the flight tube will move when the user changes between using an electron and XRay energy, this puts either the tungsten target (XRAY) or electron window (Electron) in position to treat.

The LINAC device also comprises several other components and systems. The whole system is cooled by a water cooling system (not shown in the figures). The water cooling system may be used, in particular, to cool the waveguide 104, target, and radiofrequency source 102. In order to ensure the LINAC does not leak radiation, appropriate shielding is also provided. As will be understood by the person skilled in the art, a LINAC device used for radiotherapy treatment will have additional apparatus such as a gantry to support and rotate the LINAC, a patient support surface, and a controller or processor configured to control the LINAC apparatus.

The gantry is configured to rotate the LINAC device around a patient such that radiation can be directed toward the patient from multiple angles and/or directions around the patient. LINAC device may comprise a sensor or sensing apparatus configured to provide a signal indicative of the degree to which the gantry has been rotated from which a gantry angle value can be derived.

Details of Apparatus and Sensors

Figure 2:
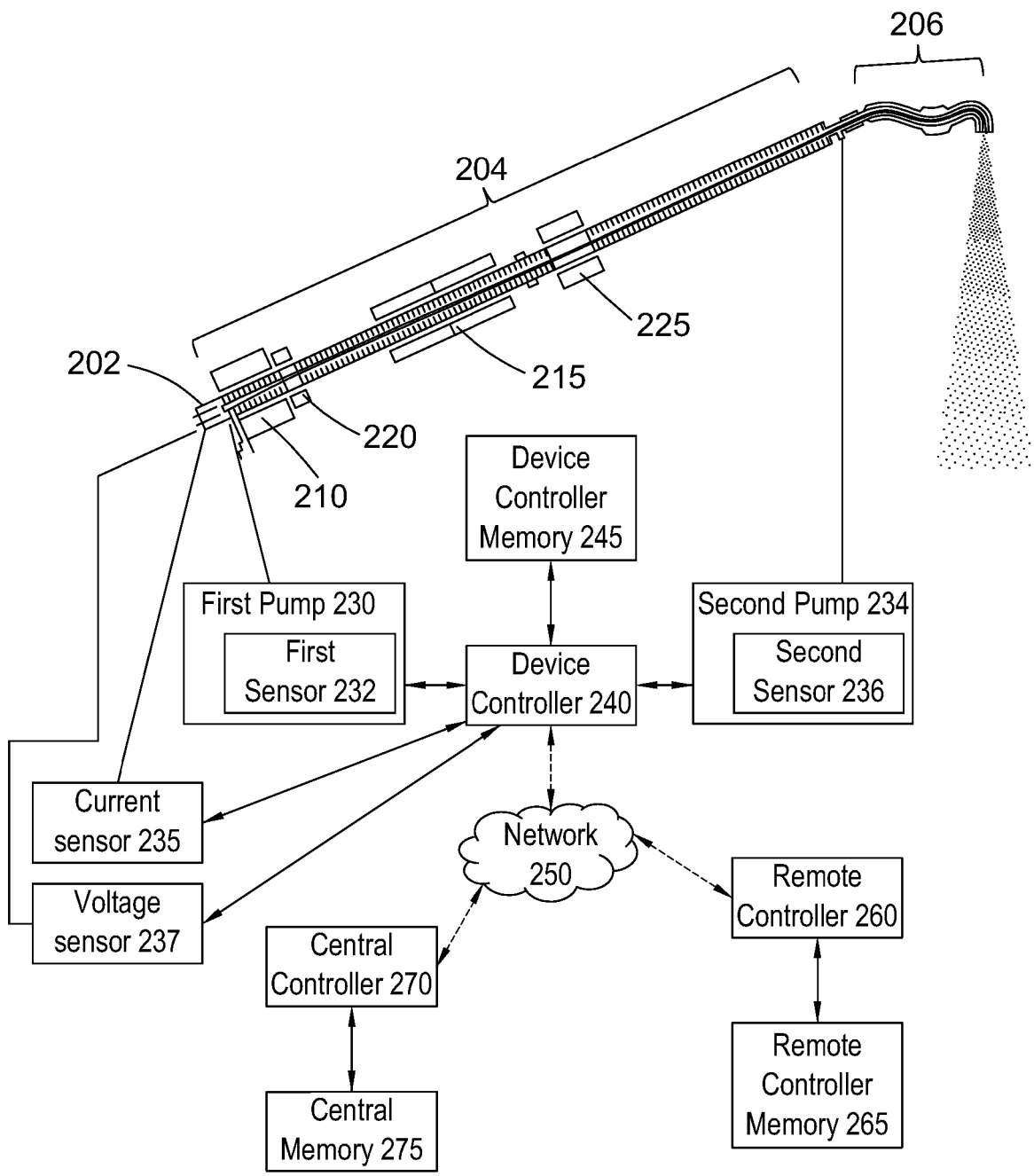
FIG. 2 depicts a system according to the present disclosure.

FIG. 2 depicts a cross-section through a vacuum tube of a LINAC. As detailed above, the vacuum tube is comprised of an electron gun 202, a waveguide 204, and a flight tube 206. The electron gun 202 is configured to inject electrons into the waveguide 204. In this example, the electron beam may be focused by a first arrangement of focusing magnets 210 and a second arrangement of focusing magnets 215. The beam is 'steered', i.e. directed, by a first arrangement of steering magnets 220 and a second arrangement of steering magnets 225. While the LINAC is in use, the electron gun 202, waveguide 204 and flight tube 206 are kept under high vacuum conditions by a vacuum system or suitable vacuum apparatus.

The LINAC also comprises a current sensor 235, e.g. an ammeter. The current sensor 235 may be comprised within the electron gun 202. The current sensor 235 is suitable for detecting, and is configured to detect, the current supplied to the electron gun, i.e. the current which passes through the cathode filament. The current sensor 235 is communicatively coupled with a device controller 240, and data relating to the electron gun current is communicated to the device controller. The current supplied to the electron gun is measured by the current sensor and communicated to the device controller 240 with a particular frequency, for example the current sensor 235 may provide a current measurement to the device controller 240 every second.

The LINAC also comprises a voltage sensor 237, e.g. a voltmeter. The voltage sensor 237 may be comprised within the electron gun 202. The voltage sensor 237 is suitable for detecting, and is configured to detect, the voltage applied to the electron gun, for example, the voltage across the cathode filament. The voltage sensor 237 is communicatively coupled with the device controller 240, and data relating to the electron gun voltage is communicated to the device controller. The voltage supplied to the electron gun is measured by the voltage sensor 237 and communicated to the device controller 240 with a particular frequency, for example the voltage sensor 237 may provide a current measurement to the device controller 240 every second.

The LINAC also comprises a gantry (not depicted) configured to rotate the LINAC device around a patient such that radiation can be directed toward the patient from multiple angles and/or directions around the patient. The LINAC device also comprises a gantry rotation sensor or sensing apparatus configured to provide a signal indicative of the degree to which the gantry has been rotated from which a gantry angle value can be derived.

In the example of FIG. 2, the vacuum system comprises two pumps coupled to either end of the vacuum tube. The region of the vacuum tube to which the first pump 230 is coupled is arranged at an opposing end of the vacuum tube to the region of the vacuum tube to which the second pump 234 is coupled. The first pump 230 is coupled with a first end of the vacuum tube at which the electron gun 202 is located. The first pump 230 may be coupled with the area of the vacuum tube adjacent the electron gun, i.e. adjacent where the electron gun 202 injects electrons into the waveguide 204. The first pump 230 is arranged and configured to remove gas molecules from the vacuum tube, and in particular is arranged and configured to remove gas molecules primarily from a first region of the vacuum tube. The first region may comprise the volume of the tube occupied by the electron gun and/or a region of the vacuum tube proximate the electron gun. The region of the vacuum tube proximate the electron gun may be described as being adjacent to or next to the electron gun. The second pump 234 is coupled with a second region of the vacuum tube located at a second end of the vacuum tube at which the flight tube 206, and hence the target, is located. The second pump 234 may be coupled with the flight tube 206 itself. The second pump 234 is arranged and configured to remove gas molecules from the vacuum tube, and in particular is arranged and configured to remove gas molecules primarily from a second region of the vacuum tube. The second region may comprise the flight tube 206 itself and/or a region of the vacuum tube proximate the flight tube 206. The region of the vacuum tube proximate the flight tube may be described as being adjacent to or next to the flight tube. For example, the second pump 234 may be coupled with the vacuum tube in a connecting region intermediate the waveguide 204 and the flight tube 206.

In an implementation, the gun pump is connected to a tube or pipe which joins the source of radiofrequency waves with the waveguide. This connecting tube or pipe introduces RF to the waveguide and joins the waveguide at a region of the vacuum tube via an elbow joint. In other words, the RF input connecting pipe or tube joins the RF input window to the waveguide. Typically, the RF input connecting pipe or tube joins, or couples with, the waveguide at a region of the waveguide adjacent the electron gun.

Figure 7:
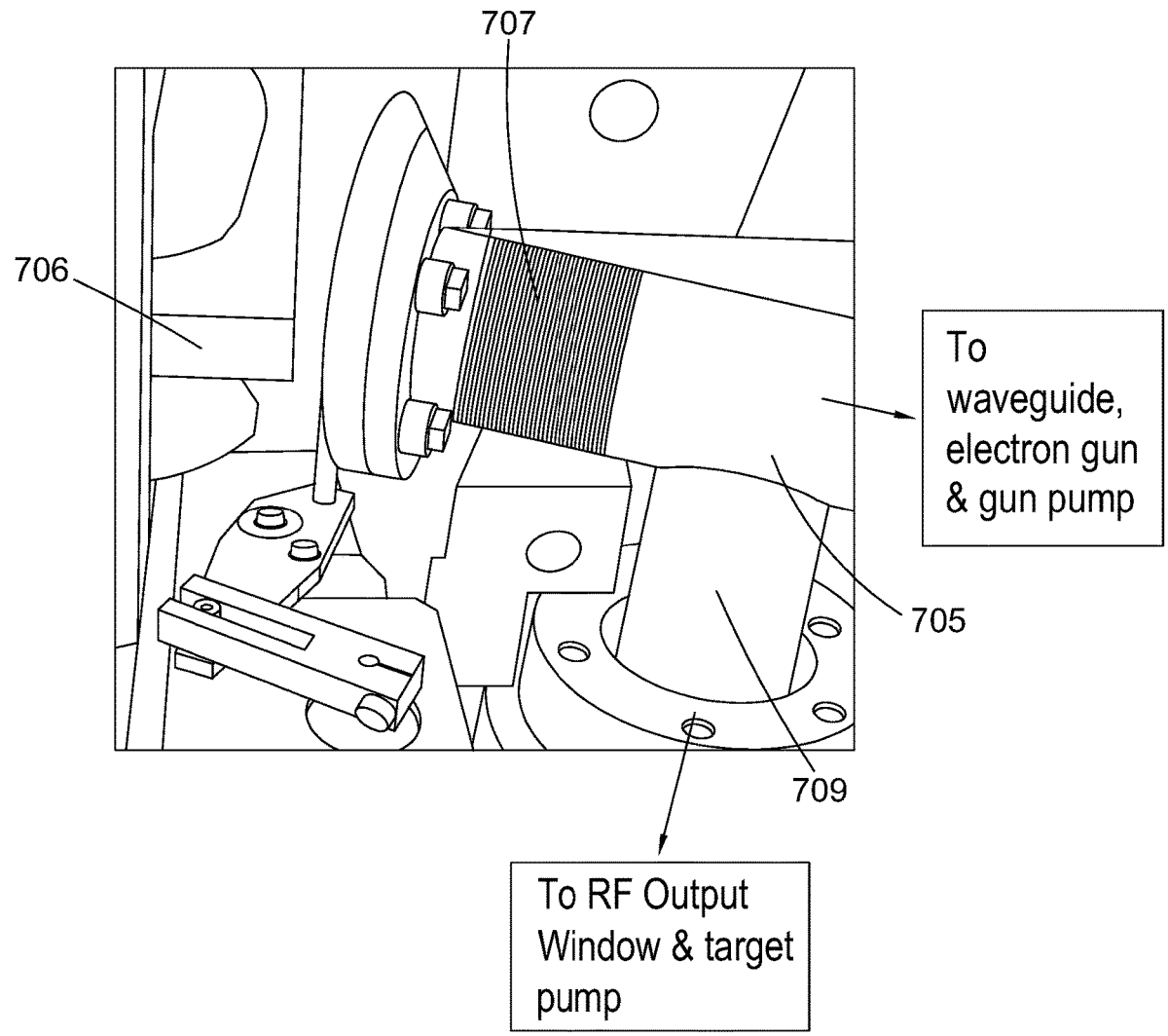
FIG. 7 depicts a region of a vacuum tube according to the present disclosure.

In an implementation, the target pump is connected to a tube or pipe through which RF exits the waveguide. This connecting tube or pipe couples a region of the waveguide with the RF output window. This RF output connecting pipe joins, or couples with, the waveguide at a region of the waveguide adjacent the flight tube, for example the drift tube. The RF input tube/pipe and the RF output tube/pipe couple with the vacuum tube via elbow joints or 'T-shaped' joints. This implementation is depicted in FIG. 7, which depicts a drift tube 707 positioned in between a waveguide (only a small part of which can be seen in the figure) and a flight tube 706 (only a small part of which can be seen in the figure). An 'elbow joint' 705 couples the drift tube 707 with an RF output connecting pipe 709 which terminates in an RF output window through which RF can exit the vacuum system. The target pump is coupled to a region of the RF exit connecting pipe between the elbow joint 705 and the RF exit window (not shown). Thus, the region of the vacuum tube to which the second pump coupled may be described as being adjacent to or next to the flight tube and/or approximate to or adjacent a drift tube which is coupled with the flight tube.

The first pump 230 may be described as being located near, or substantially near, the electron gun 202, and hence substantially near the location at which electrons enter the waveguide 204. The second pump 234 may be located near, or substantially near, the entrance to the flight tube 206, in which the target is located. The first pump 230 may therefore be referred to as a 'gun pump', and the second pump 234 may be referred to as a 'target pump'.

The first and second pumps act to create high vacuum conditions inside the electron gun 204, waveguide 206 and flight tube 206 and hence may be described as vacuum pumps. Suitable vacuum pumps include ion pumps such as diode and noble diode pumps. Ion pumps are capable of producing very low pressure inside the sealed volume of the vacuum tube. Other pumps capable of providing UHV conditions may also be used, including turbomolecular pumps and diffusion pumps.

No sensors are located inside the vacuum tube, i.e. the waveguide and flight tube, itself because there is very little space inside these components where such a sensor could be fitted. Also, any components placed inside the waveguide would affect the electromagnetic field inside the waveguide which is likely to have a negative impact on the acceleration of the electrons inside the waveguide. Further, components placed inside the vacuum tube at regions where electrons pass are susceptible to a lot of induced radiation which would not be desirable. Finally, any sensor placed inside the vacuum tube would be incredibly difficult to replace if it were to go faulty.

However, it is possible to obtain an indication of pressure inside the vacuum tube from readings provided by the vacuum pumps themselves. The readings from the pumps can be used to give an indication of the quality of the vacuum inside the vacuum tube. The first pump 230 comprises a first sensor 232 suitable for providing, and configured to provide, a signal indicative of a pressure inside the vacuum tube. As the first vacuum pump 230 is coupled with a portion of the vacuum tube substantially near the electron gun 202, the first sensor 232 is able to provide signals indicative of a pressure inside the vacuum tube proximate the electron gun 232. Thus, the first sensor 232 signals may be referred to as the 'gun vacuum' signal or gun vacuum values.

Accordingly, broadly speaking the first sensor is configured to provide signals indicative of pressure at a first region inside the vacuum tube and the second sensor is configured to provide signals indicative of pressure at a second region inside the vacuum tube. The first and second regions are located at opposing ends of the vacuum tube. In other words, the first region is closer to the first end of the vacuum tube than the second region is, and it follows that the second region is closer to the second end of the vacuum tube than the first region is.

In a manner similar to the first pump 230 and the first sensor 232, the second vacuum pump 234 comprises a second sensor 236 suitable for providing, and configured to provide, a signal indicative of a pressure inside the vacuum tube. More specifically, the second sensor 206 is configured to provide signals indicative of a pressure inside the vacuum tube proximate the target and/or the flight tube 206. Thus, signals from the second sensor 236 may be referred to as the 'target vacuum' signal or target vacuum values. More generally, the signals provided by the vacuum pumps via their respective sensors may be referred to as pressure signals. The sensors measure the pressure, i.e. vacuum level, of respective regions inside the first and second pumps. These regions are part of the same enclosed volume defined by the vacuum tube, and thus the first sensor is able to provide signals indicative of a pressure at the first end of the vacuum tube to which the first pump is coupled and the second sensor is able to provide signals indicative of a pressure at the second end of the vacuum tube to which the second pump is coupled.

More generally, the first sensor 232 and the second sensor 236 are configured to provide signals from which a pressure value can be derived, the pressure value being indicative of pressure inside the vacuum tube. The pressure value can be based on signals from either or both of the first sensor 232 and the second sensor 236.

The sensors may comprise any number of possible sensors which are suitable to measure vacuum pressure. Example sensors which may form part of a vacuum pump, and which may be used to provide signals indicative if pressure, include Pirani gauges and ionisation gauges. The vacuum pressure at the gun and target end is measured at the ion pump control unit (IPCU).

The current sensor 235 and the first and second pump 230, 234 further comprise means with which to communicate with the device controller 240. For example, the current sensor and pumps may comprise suitable processing circuitry and transmitting antennas. The current sensor and pumps are electronically and/or communicatively coupled to the device controller 240. The device controller 240 receives signals from the current sensor and pumps as they are generated, or produced, by the current sensor. The device controller 240 is electronically and/or communicatively coupled to a device controller memory 245. The device controller 240 and device controller memory 245 may be configured to store signals generated by the current sensor and pumps. The generated signals from the current sensor and pumps comprise sensor data.

The device controller 240 is communicatively coupled to a central controller 270, for example via a network 250. The device controller 240 is configured to transmit, i.e. send, the sensor data to the central controller 270 to be stored on the central controller memory 275. The central controller memory 275 may comprise a number of different servers as part of a cloud storage solution. The central controller may be communicatively coupled to a plurality of radiotherapy devices via network 250, each of which are configured to transmit signals to the central controller 270 to be stored on central memory 275. Central controller 270 is adapted and configured to process received signals and store them in a database. Processing the signals may comprise, for example, calculating and storing daily averages of particular sensor data.

The radiotherapy device has a variety of sensors, the signals/readings from which are communicated to the device controller 240. The signals may be stored in the device controller memory 245 and/or may be communicated via the network to the central controller 270. The data may be uploaded to the central controller 270 as it is generated, or may be stored on the device controller memory 245 in order to be uploaded as a batch upload, for example at regular time intervals. Alternatively, the data may be continuously gathered by the device controller 240, for example the sensor signals may be sampled every 4 seconds, optionally while the device is not delivering radiation, and data is uploaded if the data shows a particular variance from the previously uploaded data point. In a specific implementation, the data points are uploaded when there is a change of +/−0.04, and the device controller looks for a new data item once every 4 seconds, optionally while the device is not delivering radiation, and once every second while the LINAC is delivering radiation.

The data is stored in a database on central memory 275, which may comprise data from sensors, for example the data includes the current values as denoted by signals from the current sensor 235 and pressure values as denoted by signals from the first sensor 232 and/or the second sensor 236, the amount of time the electron gun has spent in the radiation mode, the degree of rotation of the gantry as denoted by signals from the gantry rotation sensor or sensing apparatus, whether or not radiation is being delivered at a particular time and the dose rate and machine output as indicated by a dosimeter or monitor chamber, as well as the water temperature at various points around the water cooling system. These types of data are given to provide examples, and the skilled person will appreciate that a modern LINAC device may be configured to generate a wealth of data from a large variety of sensors.

The data stored in the database on central memory 275 may also comprise a record of the total amount of time the electron gun has been in a radiation mode. For a particular electron gun, the received data relating to the amount of time the electron gun has spent in the radiation mode can be compiled to provide a record of the total amount of time the electron gun has been in a radiation mode.

The device controller 240 and central controller 270 are both also communicatively coupled to a remote controller 240. The remote controller 260 may access the central database, which stores information and data regarding a plurality of radiotherapy devices, through the database 250 and by using a suitable software platform. The remote controller 260 may also access the device controller 240 to obtain real-time information regarding a particular radiotherapy machine.

The device, central and remote controllers may each be described as a processor, computer, or computing device. The controllers may be connected (e.g., networked) to each other and/or to other machines in a Local Area Network (LAN), an intranet, an extranet, or the Internet. The controllers may each operate in the capacity of a server or a client machine in a client-server network environment, or as a peer machine in a peer-to-peer (or distributed) network environment. The controllers may each be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, respective controllers are illustrated, the term "controller" shall also be taken to include any collection of machines (e.g., computers) that individually or jointly execute a set (or multiple sets) of instructions to perform any one or more of the methodologies discussed herein.

The approaches of the present disclosure may be embodied on one or more of the device controller memory and the remote controller memory, or any other computer-readable medium. The medium may be a non-transitory computer-readable medium. The computer-readable medium carries computer-readable instructions arranged for execution upon a processor so as to make the controller/processor carry out any or all of the methods described herein. The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

In a LINAC device, it is generally desirable for the highest possible dose rate to be achieved for a particular energy of therapeutic radiation. The most important factor which determines the energy of the therapeutic radiation is the degree to which electrons can be accelerated by the waveguide, and this is dependent on the RF energy which is input into the waveguide. The dose rate for a particular radiation energy is dependent on the number of x-rays being emitted from the heavy metal target, which in turn is dependent on the number of electrons striking the target. Generally speaking, increasing the current supplied to the electron gun increases the number of electrons emitted from the electron gun cathode. Therefore, increasing the electron gun current increases the number of electrons which enter the waveguide. However, it is not the case that for a given radiation energy, continuously increasing the electron gun current results in a continuous increase of the dose rate. This is due to the characteristics of the waveguide and the RF energy which accelerates the electrons through the waveguide. In fact, for a given radiation energy, i.e. for a given energy of the x-rays which comprise the radiation, there is an optimal electron gun current which results in the highest possible dose rate for that radiation energy. The gun current is therefore set such that the LINAC will produce the highest dose rate achievable for that energy.

Each LINAC device is configured to produce radiation at one of several possible energies. Each of these energies has an associated optimal gun current value. The optimal gun current value for the lowest configured energy may herein be referred to as the XLOW gun current. By way of an example, a brand new LINAC machine may have a lowest possible energy of 6 MV, with a corresponding XLOW gun current of 7.95 A. By way of an alternative example, a LINAC device with a lowest configured energy of 4 MV may have an XLOW gun current of 7.85 A. The various possible radiation energies and their corresponding calibrated optimal electron gun currents are saved in the device controller memory 245 so that, when it is desired to change radiation energy e.g. during the course of treatment, or between treatments of different patients, it is possible to adjust the current applied to the electron gun 202 accordingly to ensure the highest possible dose rate is achieved. In an example, every energy has its own calibration block so that once the current has been optimised, it is saved and can be loaded again when changing between energies.

An engineer finds the optimal gun current peak at a particular energy, for example, by making 0.01 A adjustments to the gun current before saving the gun current value that causes the highest amount of dose as determined, for example, by the radiotherapy device dosimeter. The electron gun current can be regularly calibrated in this way for each device energy, for example on a monthly basis.

The dose rate or the beam energy of the LINAC machine is monitored, for example by using signals from the ionisation chambers in the treatment head of the LINAC. In an example, it is possible to monitor the energy and dose rate of the beam by monitoring the so-called hump error value. Hump is a measure of beam shape difference between the centre of the beam and the edge of the beam, and is an indication of the energy of the radiation beam. It is possible to calculate a hump value by comparing signals from a central region of an ionisation chamber with signals from an outer region of an ionisation chamber in accordance with known methods.

A so-called 'interlock value' may be applied to the measured dose rate and/or beam energy. If the measured dose rate or beam energy differs from the expected dose rate or beam energy by more than an interlock value, then the LINAC machine undergoes a safety override and will stop operating to ensure patient safety. The machine can then not be started again until the issue is fixed, or until an authorised person clears the safety override and authorises the machine for continued use. In an example, the hump value has an interlock value of 5.0%; i.e. if the measured hump value differs from the expected hump value by more than 5.0% then the LINAC machine performs a safety override. Any value of hump error other than 0.0 indicates that the beam energy has changed slightly from the previous optimal setting, and the most likely cause for this is that the gun current is 'off-peak', i.e. the current supplied to the cathode of the electron gun is not optimal. The optimal gun current can change slightly on the order of days, or weeks.

Therefore, while the optimal gun current is regularly calibrated by a field service engineer and saved in the device controller memory 245 for use with an associated LINAC energy until the next calibration, the actual current supplied to the electron gun 202 is regulated by a servomechanism or other feedback system. The servomechanism uses the optimal gun current setting as stored in the device controller memory 245 as a base current but then uses feedback relating to the dose rate obtained from the dosimetry system, for example the hump error, to make minor adjustments to the electron gun current while the radiation device is in operation.

In some implementations, for example, the servo will adjust the gun current automatically to reduce the gun difference value to 0. The gun difference value is based on the hump error, i.e. the difference between the hump outer value and the hump inner value. The servo is adjusted by the Dose Level data item, set by the field service engineer.

The current sensor may comprise any number of possible sensors which are suitable to measure the current through and voltage across the cathode filament. The cathode filament current and voltage are measured through suitable sensors and circuitry which form part of the electron gun. It will be understood that the current sensor is a sensor configured to provide a signal, or value, which is indicative of the current supplied to the filament of the cathode. Hence, the current sensor may comprise a sensor which measures the resistance of the filament, and/or the voltage across the filament, and a suitable processor and memory which uses a look-up table or other calibration data in order to provide a current value based on the signal or value provided by the current sensor.

It has presently been observed that the optimal gun currents for particular LINAC energies decrease over time as the cathode filament ages and degrades. This includes the optimal XLOW current. This may be because, as the cathode filament in the electron gun degrades over its lifetime, it requires less current to achieve a certain output of electrons. In other words, the filament becomes 'weaker' as the cathode degrades, and hence the resistance of the filament reduces. Accordingly, the current required across the filament for maximum dose rate at a particular LINAC energy decreases. This can be seen in the graph of FIG. 3.

Figure 3:
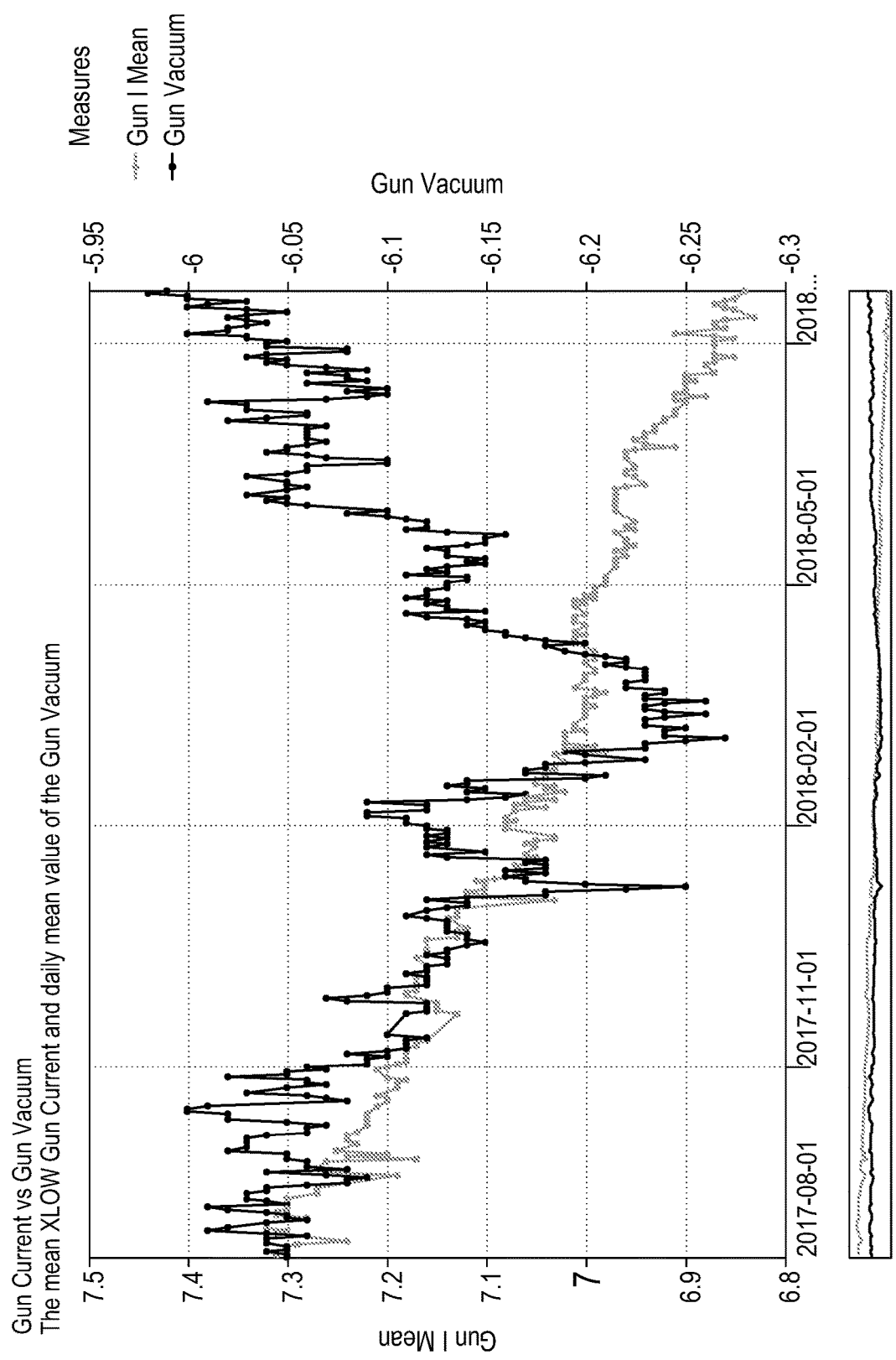
FIG. 3 depicts a graph showing data which may be used in methods of the present disclosure.

FIG. 3 shows a graph generated using data from a database of sensor values as provided by sensors on the radiotherapy device, such as the current sensor depicted in FIG. 2. The graph shows time along the X axis, current in amps along the left y axis, and pressure in arbitrary units along the right y axis.

The graph demonstrates the type of signals which may be received from the device controller and which may be accessible by a remote controller. In particular, the graph shows the general decrease of the mean XLOW gun current with time. The current values are daily averages of the actual XLOW current supplied to the electron gun. The actual current supplied to the electron gun is determined by the optimal gun current value stored in the device controller memory 245 and the servomechanism/feedback system. The daily average is calculated based on the signals provided by a current sensor which is either part of the electron gun, as described above, or alternatively which is part of the servomechanism.

The daily current averages are based on the average value of the gun current for XLOW. The gun current will fluctuate as radiation is being delivered by the radiotherapy device. As radiation is delivered, the electron gun servo monitors, for example, the change of resistance in the filament. However, it does not track this exactly and so the doserate will begin to lower as the gun drifts away from its optimal value. For example, in some implementations the servo can't deviate from the calibrated optimal value by too great a degree due to built in safety thresholds. Once the doserate has moved away from the low dose interlock (the calibrated maximum dose rate) by a certain degree or amount, for example when the doserate is 80% of the calibrated optimal doserate, then the radiotherapy device will undergo a safety interrupt, i.e. will terminate the treatment and raise a notification or alarm indicating that treatment was halted for patient safety because the delivered doserate has fallen too far below the maximal value. As the gun current drifts further off peak, i.e. away from the optimal value, the frequency of these interrupts and alarms will increase. It is the existence or increased frequency of these interrupts and alarms that, in prior methods, has been relied upon to alert field engineers that the electron gun should be scheduled for repair or replacement.

The unit of the right y axis is a semi-arbitrary unit which is derived from vacuum pressure readings from pump sensors. For a particular ion pump, the voltage of the ion pump is related to the $\log_{10}$ of the current absorbed by the pump as follows:

$$V_{rec-out} = 1.35 \cdot \log 10 I_{out} + 6.77$$

In an implementation, the vacuum pressure recorded on the ion pump control unit (IPCU) is then converted to give values between the range of −4.49 and −6.8, where −4.49 relates to a vacuum pressure of 1.55E-04 mBar and −6.8 is 5.60E-08 mBar. A reading of −5.50 is therefore 4.64E-06 mBar.

Figure 6:
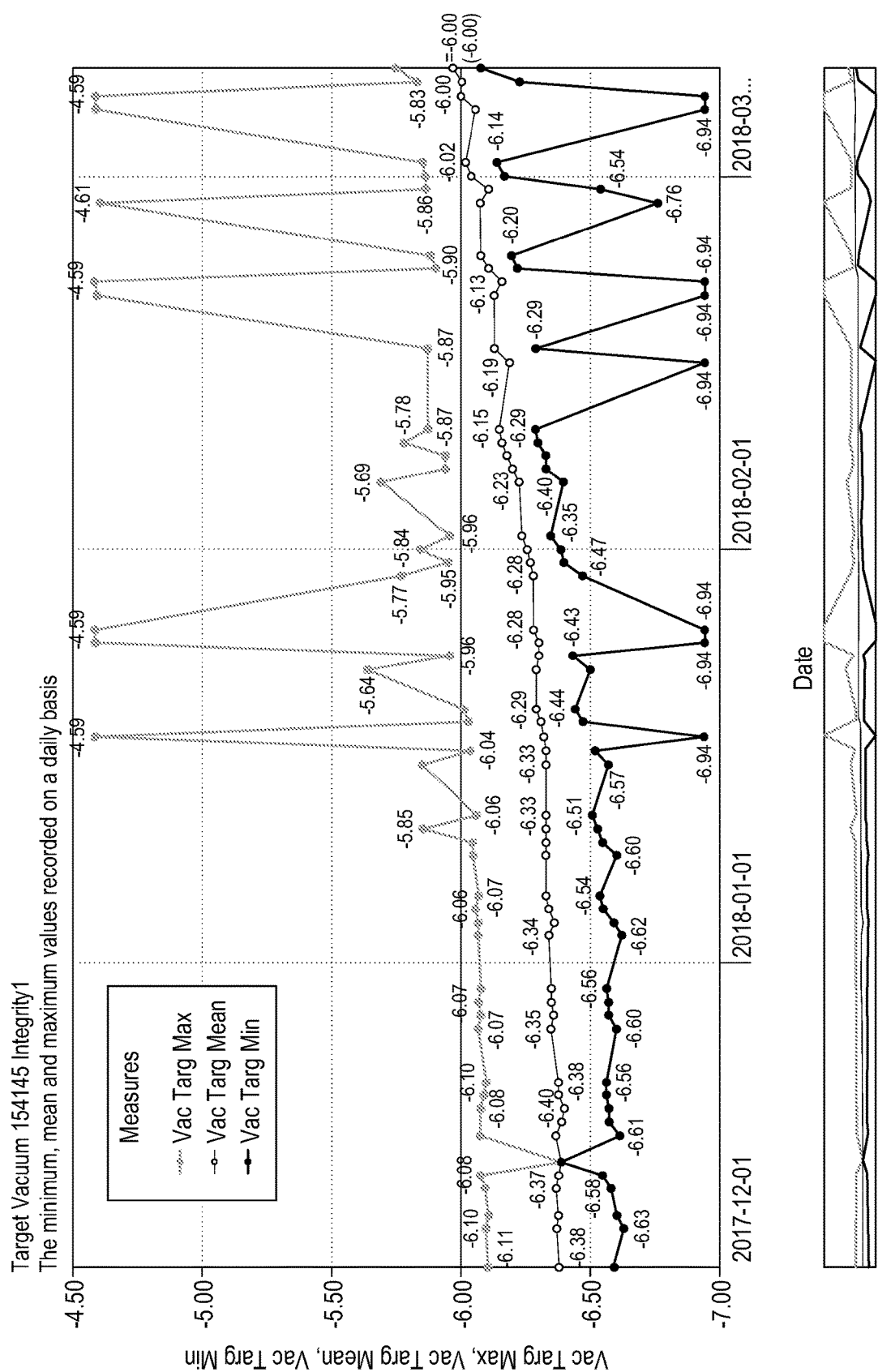
FIG. 6 depicts a graph showing vacuum or pressure values generated by a sensor according to the present disclosure.

FIG. 6 shows a graph generated using data from a database of sensor values as provided by sensors such as the sensors 232, 236 depicted in FIG. 2. The graph shows time along the X axis and pressure along the Y axis. The unit of the y axis is a semi-arbitrary unit which is derived from the vacuum pressure readings from each pump sensor. For a particular ion pump, the voltage of the ion pump is related to the $\log_{10}$ of the current absorbed by the pump as follows:

$$V_{rec-out} = 1.35 \cdot \log 10 I_{out} + 6.77$$

In an implementation, the vacuum pressure recorded on the ion pump control unit (IPCU) is then converted to give values between the range of −4.49 and −6.8, where −4.49 relates to a vacuum pressure of 1.55E-04 mBar and −6.8 is 5.60E-08 mBar. A reading of −5.50 is therefore 4.64E-06 mBar.

The graph shows signals received from the target vacuum pump as generated by the target vacuum sensor. The graph demonstrates the type of signals which may be received form the device controller and which may be accessible by a remote controller. A similar graph may be generated for the gun pump. The line which is generally uppermost on the graph is the target pump daily maximum reading. Each data point is the maximum value for a particular day, i.e. the maximum value for a particular data between a period from 00:00 to 23:59. The line which is generally lowermost on the graph is the target pump daily minimum reading, with each data point being the minimum value that day. Finally, the line which is generally between the maximum and minimum lines is the daily average line. Each data point on this line is the average target pump value for a particular day.

Specific Methods

Figure 4:
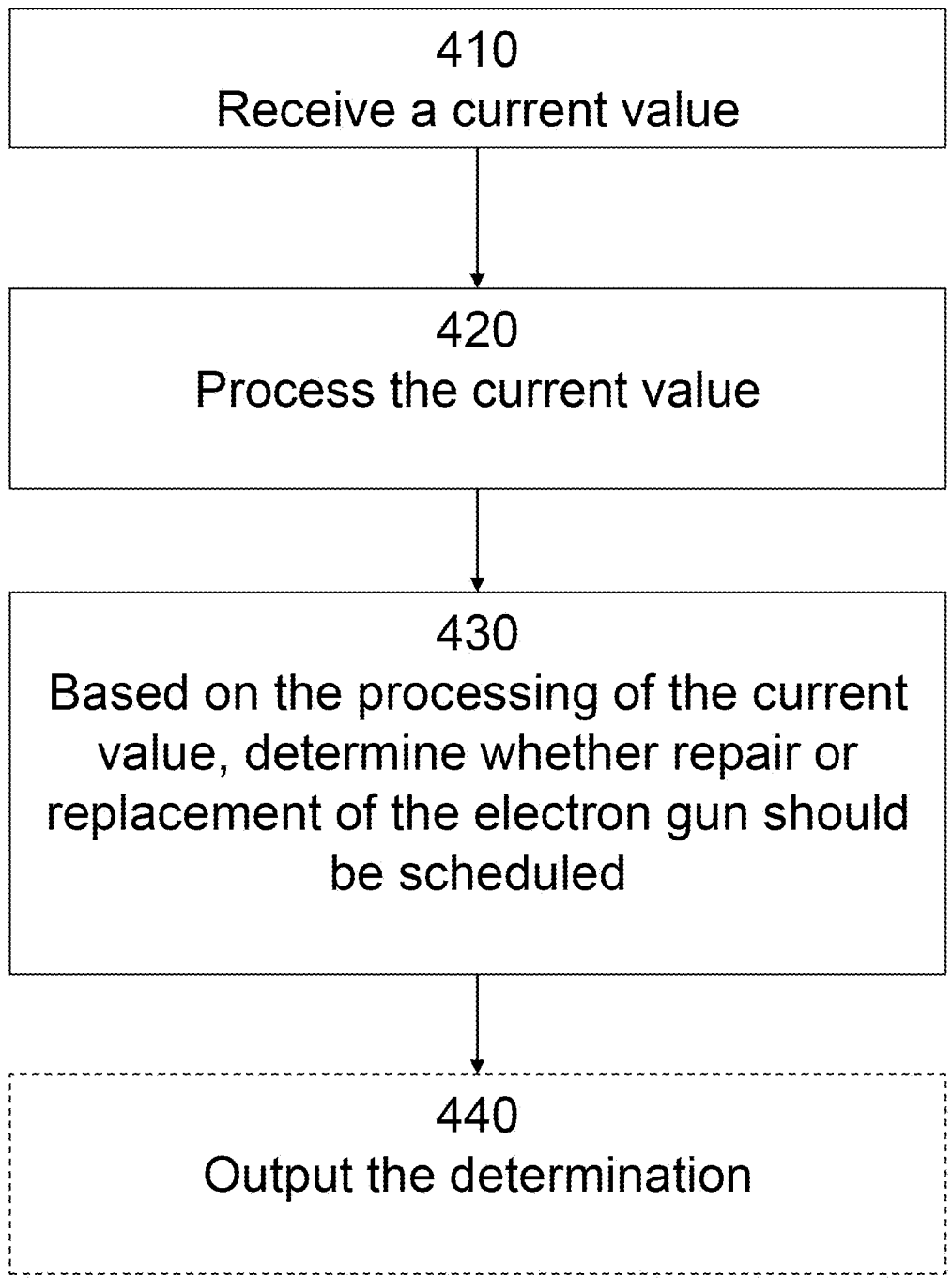
FIG. 4 is a flowchart which depicts a method according to the present disclosure.

Reference is now made to the method depicted in the flowchart of FIG. 4. At step 410, a current value is received. The current value is derived from signals from the current sensor. As set out above, there is an optimal gun current value for a particular radiation energy, however the actual current supplied to the electron gun may vary slightly in the vicinity of this optimal value as the radiation beam is applied and because the current supplied to the electron gun is controlled by a servomechanism. Therefore, the current measured by the current sensor 235 and received by the device controller 240 varies as the LINAC operates. The current value received at step 410 may be an average of signals or values received from the current sensor over a time period. In other words, the current value may be an average current supplied to the electron gun over the time period. Preferably, the time period is a day, such that the current value is a daily average of the current supplied to the electron gun.

The method may further comprise deriving the current value by calculating or otherwise determining the average of the received signals from the current sensor 235 over the time period.

At step 420, the current value is processed. The processing of the current value is described in more detail in relation to FIG. 5, though in a preferred embodiment the processing of the current value comprises determining whether the current value meets at least one threshold criterion, and determining whether the current value has changed by a threshold amount or more in a particular time period.

At step 430, based on the processing of the current value, it is determined whether repair or replacement of the electron gun should be scheduled. In an example, it is determined that repair or replacement should be scheduled if the determinations at step 420 described above are positive, i.e. if the current value meets the at least one threshold criterion and the current value has changed by at least the threshold amount in a particular time period.

By way of a specific example of steps 410, 420, and 430, signals relating to the current supplied to the cathode filament are received at the device controller 240 from the current sensor 235, and are communicated to the central controller 270 to be stored in the central memory 275. The central controller 270 receives a daily average of the current by calculating, or determining, the daily average based on the received current values. The daily average of the current is then processed; in particular it is determined whether the average current for a particular radiation energy (for example the XLOW gun current) is below 6.90 A. It is also determined, as part of the processing of the averaged current value, whether the mean XLOW gun current has reduced by 0.05 A or more in the last 30 days. Based on the processing of the average current value, it is determined whether repair or replacement of the electron gun should be scheduled. For example, if the above-described determinations are positive, it is determined that the electron gun should be repaired or replaced.

At step 440, the determination at step 430 of whether the repair or replacement should be scheduled is outputted. This step is optional. Outputting the determination may comprise displaying an indication of the determination on a display screen. In response to this indication, the repair or replacement of the electron gun can be scheduled at the next available service point, or at a convenient time for the machine owner, for example during planned machine down time. Outputting the determination may also comprise issuing an alert or notification detailing the determination to a field service engineer. The alert may comprise information regarding how to test the electron gun for faults, and may also comprise information detailing how to replace the electron gun, or how to repair the electron gun for example by replacing the cathode filament. Outputting the determination may also comprise issuing a communication, alert, or otherwise contacting the owner of the radiotherapy device in order to inform them of the issue and to schedule the repair or replacement.

Figure 5:
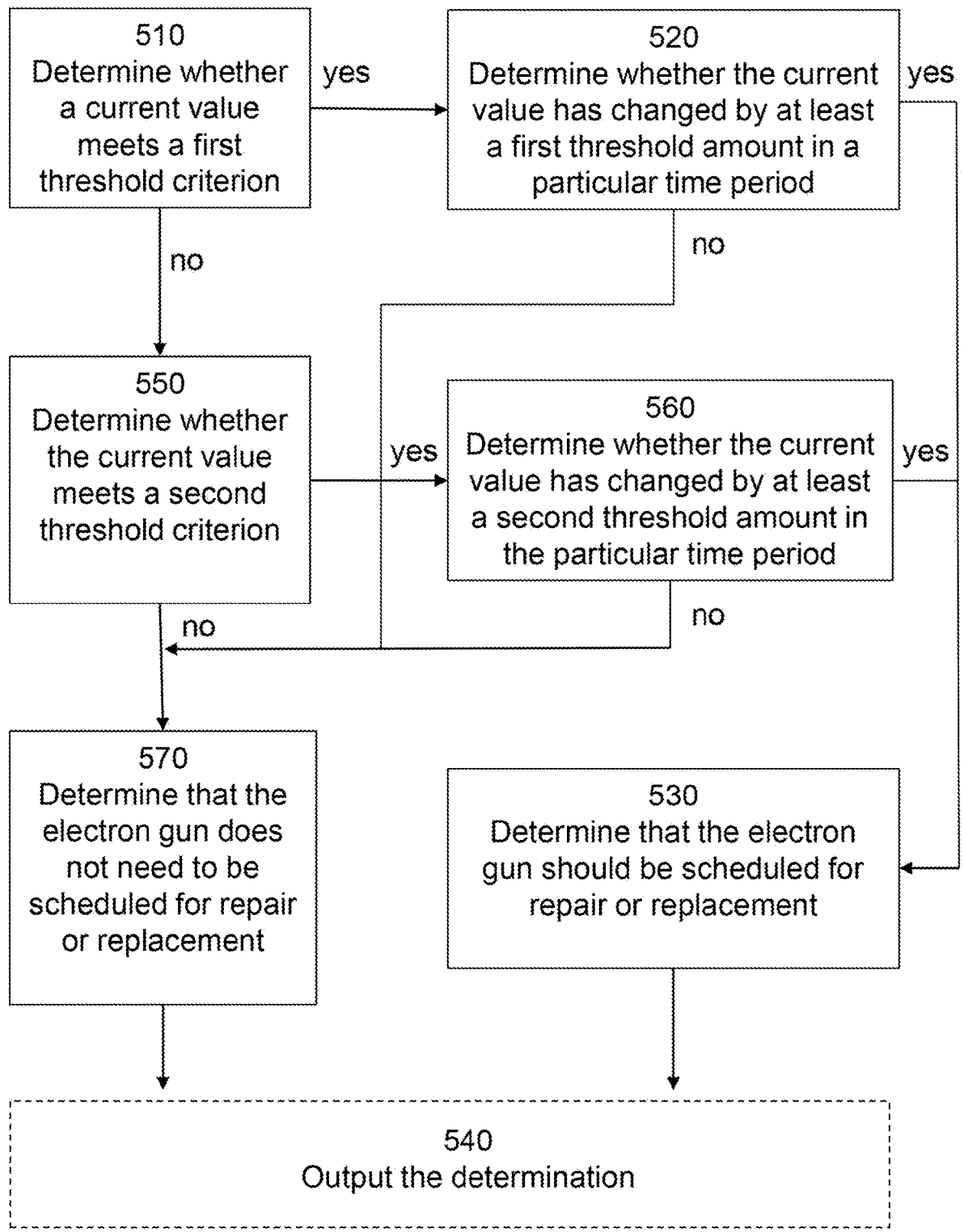
FIG. 5 is a flowchart which depicts a method according to the present disclosure.

In an example, once the prediction criteria described herein and set out in the flowchart of FIG. 5 have been met, a report is generated and an alert is raised. This alert is then sent to the relevant service team and they will plan a replacement, typically within the next 3-6 weeks or align with a planned maintenance activity.

In a preferred embodiment, the device controller 240 receives signals from the current sensor and transmits them to the remote controller 260. The central controller 270 receives the signals and then derives the current value, for example by calculating the average current value from the signals over a time period. The average current value is stored on the central controller memory 270. Processing of the current value then takes place when the remote controller 260 accesses the central memory 275 via the network 250. However, at least some of the steps, and in some examples all of the steps, displayed in FIG. 4 may be performed on the device controller 240. It will be appreciated that any combination of the device controller 240 central controller 270 and remote controller 260 may be used to perform the disclosed methods.

Reference is now made to the flowchart of FIG. 5. The flowchart shows steps 420, 430 and the optional step of 440 in greater detail, and in particular shows the processing of the current value in greater detail. At step 510, it is determined whether the received or derived current value meets a first threshold criterion. In a particular example, checking whether the first criterion is met comprises determining that the current value, e.g. the mean XLOW gun current value for a particular day, is below a first threshold value, for example a first threshold average current value. If so, the criterion is met. In a particular example, it is determined whether the mean XLOW gun current is below 6.90 A.

If the current value meets the first threshold criterion, then the process proceeds to step 520. At step 520, it is determined whether the current value has changed by at least a first threshold amount in a particular time period. The first threshold amount can be described as a first particular amount. In a particular example, the first threshold amount is 0.05 A and the particular time period is 30 days, such that it is determined whether the mean XLOW gun current has reduced by 0.05 A or more in the last 30 days. If so the criterion is met.

If the current value has changed by the threshold amount in the time period, then it is determined, at step 530, that the electron gun should be scheduled for repair or replacement. This determination may be outputted at step 540 in a manner similar to the outputting at step 440.

If at step 520 or step 560 it is determined that the current value has not changed by the first or second threshold amount, as appropriate, in the particular time period, then the replacement/repair criteria are not fulfilled and it is determined at step 570 that the electron gun should be not be repaired or replaced.

If at step 510 it is determined that the current value does not meet a first threshold criterion, e.g. the daily average of the XLOW electron gun current is not less than 6.90 A, then at step 550 it is determined whether the current value meets a second threshold criterion. In an example, checking or determining whether the second threshold criterion is met may comprise determining whether the current value is below a second threshold value, for example a second average current value. In a particular example, checking the second threshold criterion is met comprises determining that the current value, e.g. the mean XLOW gun current value for a particular day, is below a second threshold value. In a particular example, it is determined whether the mean XLOW gun current is below 7.20 A.

Step 550 may alternatively or additionally comprise determining that the current value is within a threshold range of values, where the threshold range is defined by an upper range value and a lower range value. The lower range value may be equal to the first threshold value. For example, it may be determined at step 550 whether the mean XLOW gun current for a particular day is between 6.90 amps and 7.20 amps.

If the current value meets the second threshold criterion, then the process proceeds to step 560. At step 560, it is determined whether the current value has changed by at least a second threshold amount in the particular time period. The second threshold amount can be described as a second particular amount. In a particular example, the second threshold amount is 0.10 A and the particular time period is 30 days, such that it is determined whether the mean XLOW gun current has reduced by 0.10 A or more in the last 30 days.

If the current value has changed by the second threshold amount in the time period, then it is determined, at step 530, that the electron gun should be scheduled for repair or replacement. This determination may be outputted at step 540 in a manner similar to the outputting at step 440.

It has been noted by the inventors that, as the electron gun in a LINAC reaches the end of its useful life, the rate of change of the optimal current increases. In other words, the current which must be supplied to the cathode filament for a particular LINAC energy in order to attempt to obtain optimal dose rate decreases more rapidly as the electron gun reaches the end of its life. Using thresholds relating to whether the current value has changed by a particular amount in a time period, i.e. which relate to the rate of change of the current value, allows calibration errors to be accounted for, and ensures that only devices which are accelerating toward failure are flagged for repair or replacement. It has been noted that devices operating with very low gun currents may still be capable of operating within acceptable operating parameters, e.g. be capable of providing an acceptable dose rate. The use of thresholds relating to the rate of change of the gun current help to ensure that unnecessary service visits and/or repairs and replacements are not occasioned.

In certain implementations, the first threshold at step 510 is a lower threshold than the second threshold at step 550. In combination with this, the first threshold amount at step 520 is smaller than the second threshold amount at step 560. These factors together mean that electron guns which have a lower current value, which is itself indicative that the filament has degraded to a greater degree, need meet a lower current 'rate' criteria in order to be classified as an electron gun that should be repaired or determined.

In a specific example, determining whether the first criterion is met comprises checking that the XLOW electron gun current is less than 6.90 A, and determining whether the second criterion is met comprises checking that the XLOW electron gun current is less than 7.2 A. With reference to the graph of FIG. 3, on 2017-08-01, the process detailed in the flowcharts of FIGS. 4 and 5 is followed for a particular radiotherapy device comprising a LINAC and electron gun. With reference to the graph, the current value on 2017-08-01 is around 7.31 A. Accordingly, neither the first or second threshold criterion is met at steps 510, 550, and it is determined at step 570 that the electron gun does not need to be scheduled for repair or replacement.

The same process is followed on 2017-11-01, on which date the current value is 7.19 A. In this scenario, 7.19 A is greater than 6.90 A and accordingly the first threshold criterion at step 510 is not met. However, the current value is lower than 7.2 A, and accordingly the second threshold criterion is met at step 550. However, upon review of the current value previous 30 days, which in this example is the relevant particular time period, it is determined that the current value has not changed by the second threshold amount of 0.10 A. Accordingly, it is determined at step 570 that the electron gun does not need to be replaced.

The same process is followed on 2018-08-01. The gun current value is 6.87 A, and thus the gun current value does not meet the first threshold criterion at step 510. Upon reviewing the previous 30 days of data, it is determined at step 520 that the value has changed by at least the first threshold amount of 0.05 A, and thus that the electron gun should be scheduled for repair or replacement. Following this determination, an alert is raised and/or a message is sent to the relevant repair team to ask them to schedule an on-site visit to the radiotherapy device comprising the electron gun. The team are able to determine whether the electron gun needs either repair or replacement.

The methods of the present disclosure may be performed on a regular basis, for example daily, in order to continuously monitor whether the electron gun of a radiotherapy device should be repaired or replacement, or at least scheduled for repair or replacement.

It will be appreciated that while a specific order of steps is set out in FIG. 5, these steps may be performed in a different order.

It will be appreciated that while reference is made to the XLOW current, i.e. the current supplied to the cathode for the lowest configured energy of the LINAC, the current while the LINAC is operating at any particular energy may be used. For machines manufactured by the applicant, XLOW is typically 6 MV, in 85% of machines, and 6 MV is used more than any other energy. In fact, around 85% of all clinical use is with 6 MV. The advantage of using the current at the XLOW energy is therefore that this is the energy most used by the LINAC machine and hence monitoring the current at this energy will produce the most data items for analysis.

Reference is now made to the method depicted in the flowchart of FIGS. 8*a* and 8*b*. The method identifies whether the electron gun of a radiotherapy device has poor gun life of due to vacuum issues by analysing various parameters.

At step 810, a current value is received in a similar manner to step 410 described above. The current value is derived from signals from the current sensor. As set out above, there is an optimal gun current value for a particular radiation energy, however the actual current supplied to the electron gun may vary slightly in the vicinity of this optimal value as the radiation beam is applied and because the current supplied to the electron gun is controlled by a servomechanism. Therefore, the current measured by the current sensor 235 and received by the device controller 240 varies as the LINAC operates. The current value received at step 810 may be an average of signals or values received from the current sensor over a time period. In other words, the current value may be an average current supplied to the electron gun over the time period. Preferably, the time period is a day, such that the current value is a daily average of the current supplied to the electron gun. The method may further comprise deriving the current value by calculating or otherwise determining the average of the received signals from the current sensor 235 over the time period.

At step 820, the current value is processed. In a preferred embodiment, the processing of the current value comprises determining whether the current value meets at least one first threshold criterion. Optionally, this comprises determining that the current value has fallen below a threshold current value, for example below 7.35 A.

Exceeding this first threshold criterion may give a warning that the electron gun is potentially around 60% of the way through its life time. This threshold criterion may also give around three months' warning ahead of a potential failure of the electron gun, allowing a service activity to be aligned with a planned maintenance activity and to also allow time to prepare the additional parts or equipment required, such as an Ion Pump.

By way of a specific example of steps 810 and 820, signals relating to the current supplied to the cathode filament are received at the device controller 240 from the current sensor 235 and are communicated to the central controller 270 to be stored in the central memory 275. The central controller 270 receives a daily average of the current by calculating, or determining, the daily average based on the received current values. The daily average of the current is then processed; in particular it is determined whether the average current for a particular radiation energy (for example the XLOW gun current) is below 7.35 A.

At step 830, it is determined whether a total amount of time the electron gun has been in a radiation mode meets at least a second threshold criterion. The determination may be made by accessing data stored in the database on central memory 275 which comprise a record of the total amount of time the electron gun has been in a radiation mode. Alternatively, at least one of the device controller memory or remote controller memory may be accessed to obtain data relating to a total amount of time the electron gun has been in a radiation mode when it is stored at either or both of these locations. In a preferred embodiment, it is determined that the total amount of time the electron gun has been in a radiation mode is less than a threshold time period, optionally, wherein the time period is 600 hours.

Meeting the second threshold criterion may indicate that gun life for the electron gun is shorter than expected, particularly when considered in conjunction with the first threshold criterion. If both first and second criteria are met, it is indicative of the electron gun degrading sooner than expected. This could be indicative of an issue with the vacuum of the vacuum tube.

At optional step 840, a pressure value is received. The pressure value is based on signals received from at least one of the first and second sensors 232, 236 associated with the first and second pumps 230, 234. As detailed elsewhere herein, the first and second sensor are configured to provide signals indicative of pressure inside the vacuum tube. More specifically, the first sensor is configured to provide signals indicative of a pressure inside the vacuum tube proximate the electron gun, and the second sensor is configured to provide signals indicative of a pressure inside the vacuum tube proximate the flight tube and/or the target. The first signals are processable to provide a first value indicative of pressure at the first end of the vacuum tube, and the second signals are processable to provide a second value indicative of pressure at the second end of the vacuum tube. The first value is derived from signals from the first sensor in any of the manners disclosed herein. Similarly, the second value is derived from signals from the second sensor in any of the manners disclosed herein.

The signals are received at one or more of the device controller and the remote controller. For example, the signals may be received at the device controller and stored in the device controller memory as part of a database/log of received signals from that particular radiotherapy machine.

The signals may also be received at the remote controller and stored in the remote controller memory as part of a database. The remote controller and memory are configured to respectively access and store data from a plurality of radiotherapy machines connected to the remote controller via the network. The received signals may take a variety of forms. For example, signals may be received from either or both the first and second sensors on a regular basis. In this example, the first pump communicates the reading from the first sensor and the second pump communicates the reading from the second sensor to the device controller on a regular basis, for example every 4 seconds.

The pressure value received at step 840 may be an average of signals received from either or both the first and second sensors over a time period. In other words, the pressure value may be an average pressure in the vacuum tube over the time period. Preferably, the time period is a week, such that the pressure value is a weekly average of the pressure in the vacuum tube. The method may further comprise deriving the pressure value by calculating or otherwise determining the average of the received signals from either or both the first and second sensors over the time period.

At optional step 850, the pressure value is processed. In a preferred embodiment, the processing of the pressure value comprises determining whether the pressure value meets at least one third threshold criterion. Optionally, this comprises determining that the pressure value has fallen below a threshold pressure value, for example below −6.15 (5.03E-07 mBar).

Exceeding this threshold suggests that the vacuum system is not performing as well as it should, either due to cleanliness, a vacuum leak or poorly performing pumps. In general terms to it shows that the vacuum quality is the likely cause for the short gun life.

The pressure value obtained for any particular radiotherapy device can be reviewed against a history of pressure values for the device. For example, if 'Machine A' has a vacuum of −6.14 (5.19E-07 mBar) in August 2019, checking the full vacuum history reveals that, in August 2017, the pressure value was recorded as −6.35 (2.54E-07 mBar). This machine is therefore capable of better vacuum and so the possibility of improving the vacuum should be investigated further. Should the obtained value be the same as the historical values, the may indicate that it will take a longer service activity to clean/de-contaminate the vacuum system.

By analysing the history of pressure values for the device, any seasonal variation in pressure values, where the better pressure values are recorded in winter months and worse values recorded in the summer months, can be factored in. The vacuum system tends to work better in cold conditions as contamination is less likely to be disturbed. Typically, the main contaminate will be water vapour. This is disturbed at higher temperatures whereas it is less reactive at cold temperatures. The contaminates also react when the beam is first turned on and RF is sent down the waveguide, this can cause a vacuum spike before normalising.

At step 860, based on at least the processing of the current value, it is determined whether maintenance of the radiotherapy device should be scheduled. In an example, it is determined that maintenance of the radiotherapy device should be scheduled if the determinations at steps 820 and 830 (and optionally 850) described above are positive, i.e. if the current value meets the at least one threshold criterion and a total amount of time the electron gun has been in a radiation mode meets at least a second threshold criterion (and optionally the pressure value meets at least one third threshold criterion).

At step 870, the determination at step 860 of whether maintenance of the radiotherapy device should be scheduled is outputted. This step is optional. Outputting the determination may comprise displaying an indication of the determination on a display screen. In response to this indication, the maintenance of the radiotherapy device can be scheduled at the next available service point, or at a convenient time for the machine owner, for example during planned machine down time. Outputting the determination may also comprise issuing an alert or notification detailing the determination to a field service engineer.

The alert may comprise information regarding how to test the radiotherapy device for a vacuum leak introduced after a previous replacement of the electron gun or contamination due to frequent gun changes and little conditioning time. The alert may also comprise how to fix a vacuum leak or how perform a bake out procedure to fix a contamination issue. Outputting the determination may also comprise issuing a communication, alert, or otherwise contacting the owner of the radiotherapy device in order to inform them of the issue and to schedule maintenance of the radiotherapy device.

In an example, contamination can be detected by identifying that the pressure value starts at a first value (e.g. −6.09 or 6.07E-07 mBar) before a decline to a lower second value (e.g. −5.93 or 1.07E-06 mBar) is detected after the after the radiotherapy device has warmed up which is indicated by the increasing water temperature. The electron gun then begins operating in a radiation mode and the vacuum degrades further and continues to do so until the pressure value it is detected as settling at an even lower third value (e.g. −5.81 or 1.60E-06 mBar). This behaviour is an indication of contamination as the vacuum performance degrades as the temperature increases.

In an example, a vacuum leak can be detected by identifying that the pressure value starts at a first value (e.g. −5.90 or 1.17E-06 mBar). Once the radiotherapy device has warmed up and the electron gun has begun operating in a radiation mode, a vacuum change which meets a threshold is detected (e.g. which exceeds a certain minimum reduction in pressure value, which could be, for example, a 0.10 change) and this is indicative of a vacuum leak. If the first value is −5.90 (1.17E-06 mBar) and, after the machine has completed a first operation in a radiation mode, if the pressure value is detected to be between −5.80 (1.65E-06 mBar) to −5.90 (1.17E-06 mBar), This could be indicative of a vacuum leak. Should the vacuum pressure value be detected to be less than −5.80 (1.65E-06 mBar) at this point. This could be a combination of a vacuum leak and contamination or more severe contamination.

In an example, once the criteria described herein and set out in the flowchart of FIGS. 8a and 8b have been met, a report is generated and an alert is raised. This alert is then sent to the relevant service team and they will plan maintenance of the radiotherapy device.

In a preferred embodiment, the device controller 240 receives signals from the current sensor and one or both of the first and second sensors and transmits them to the remote controller 260. The central controller 270 receives the signals and then derives the current value, for example by calculating the average current value from the signals over a time period, and the pressure value, for example by calculating the average pressure value from the signals over a time period. The average current value and the average pressure value are stored on the central controller memory 270. Processing of the current value and the pressure value then takes place when the remote controller 260 accesses the central memory 275 via the network 250. However, at least some of the steps, and in some examples all of the steps, displayed in FIGS. 8a and 8b may be performed on the device controller 240. It will be appreciated that any combination of the device controller 240 central controller 270 and remote controller 260 may be used to perform the disclosed methods.

Reference is now made to the method depicted in the flowchart of FIGS. 9a and 9b. The method may begin from optional step 910 or step 920. At optional step 910, a notification is received of a fault in a radiotherapy device. The radiotherapy device may be a LINAC device. The notification may indicate that the radiotherapy device has begun operating outside of its normal operating parameters. The generating of the notification is described in more detail in relation to FIG. 10. The notification may be triggered when one or more conditions are met. A possible condition that may cause a fault notification to be issued may be that a received current value and/or a received second voltage value are determined to respectively meet a third and a fourth threshold.

At step 920, voltage values during a rotation of the gantry are received. This step may be undertaken in response to receiving the notification of a fault at step 310 or may be otherwise taken in order to begin the process of determining the nature of a fault. For example, the process can be manually started in response to an operator becoming aware that a radiotherapy machine has a fault. Preferably, a series of voltage values are taking during a gantry rotation at various points in the gantry rotation while the electron gun is in an inactive or standby mode. In this manner, any change in received voltage values across the gantry rotation can be subsequently identified as follows.

The signals are received from the voltage sensor 237 during a rotation of the gantry. As detailed elsewhere herein, the voltage sensor 237 is configured to provide signals indicative of voltage applied to the electron gun. The signals are processable to provide voltage values indicative of the voltage applied to the electron gun at various points in time during the gantry rotation. The voltage values are derived from signals from the voltage sensor in any of the manners disclosed herein.

The signals are received at one or more of the device controller and the remote controller. For example, the signals may be received at the device controller and stored in the device controller memory as part of a database/log of received signals from that particular radiotherapy machine. The device controller memory also stores a record of any faults identified by the device controller.

The signals may also be received at the remote controller and stored in the remote controller memory as part of a database. The remote controller and memory are configured to respectively access and store data from a plurality of radiotherapy machines connected to the remote controller via the network. The received signals may take a variety of forms. For example, signals may be received from the voltage sensor on a regular basis. In this example, the voltage sensor communicates signals to the device controller on a regular basis, for example every 4 seconds during the gantry rotation.

At step 930, the voltage values are processed. In a preferred embodiment, the processing of the voltage values comprises determining whether the voltage values meet at least one first threshold criterion. Optionally, this comprises determining whether the voltage values vary by at least a threshold amount during the rotation of the gantry, for example by 0.2V. Optionally, this comprises determining whether the voltage values vary by at least a threshold amount of 0.05V. This change in voltage values is indicative of movement of one or more components of the electron gun during rotation of the gantry as a result of the effects of gravity on loose components. For example, a loose carrier for the cathode of the electron gun could cause the variance in voltage values. There could also be loose connections on the gun body or issues with the gun isolation transformer which give rise to the determined variation in voltage.

Exceeding the first threshold shows that the resistance of the filament of the cathode of the electron gun is changing during gantry rotation, the higher the variation the more likely the machine is to be unstable during clinical treatment.

At optional step 940, the voltage values are processed, this time to determine whether the electron gun is in a standby mode during the rotation of the gantry by determining whether the voltage values meet at least one second threshold criterion. Optionally, this comprises determining whether the voltage values are less than a first threshold voltage value, for example 15V.

At optional step 950, a gantry angle value, derived from signals provided by the gantry rotation sensor, is received for each of the received voltage values.

The signals are received from the gantry rotation sensor. As detailed elsewhere herein, the gantry rotation sensor is configured to provide signals indicative of the degree to which the gantry has been rotated. The signals are processable to provide gantry angle values indicative of the degree to which the gantry has been rotated.

The signals are received at one or more of the device controller and the remote controller. For example, the signals may be received at the device controller and stored in the device controller memory as part of a database/log of received signals from that particular radiotherapy machine. The device controller memory also stores a record of any faults identified by the device controller.

The signals may also be received at the remote controller and stored in the remote controller memory as part of a database. The remote controller and memory are configured to respectively access and store data from a plurality of radiotherapy machines connected to the remote controller via the network. The received signals may take a variety of forms. For example, signals may be received from the gantry rotation sensor on a regular basis. In this example, the gantry rotation sensor communicates signals to the device controller on a regular basis, for example every 4 seconds. Alternatively, the signals may be received every time the voltage sensor communicates signals to the device controller to provide a gantry angle value which corresponds to a voltage value derived from the signals provided by the voltage sensor. In this manner, each voltage value is provided with a corresponding gantry angle value.

At optional step 960, the gantry angle values are processed. In a preferred embodiment, the processing of the gantry angle values comprises determining whether the rotation of the gantry has met at least one fifth threshold criterion. Optionally, this comprises determining whether the rotation of the gantry exceeds a threshold degree of rotation, for example 90 degrees. Optionally, this comprises determining whether the rotation of the gantry exceeds a threshold degree of rotation, for example 360 degrees.

At step 970, based on at least the processing of the voltage values, it is determined whether the nature of the fault is associated with the electron gun. In an example, it is determined that the nature of the fault is associated with the electron gun if the determinations at steps 930 (and optionally 940 and 960) described above are positive, i.e. if the voltage values meet the at least a first threshold criterion (and optionally the voltage values meet the at least a second threshold criterion and/or the rotation of the gantry has met the at least a fifth threshold criterion).

At step 980, the determination at step 970 of whether the nature of the fault is associated with the electron gun is outputted. This step is optional. Outputting the determination may comprise displaying an indication of the determination on a display screen. In response to this indication, the maintenance of the radiotherapy device can be scheduled to fix the fault at the next available service point, or at a convenient time for the machine owner, for example during planned machine down time. Outputting the determination may also comprise issuing an alert or notification detailing the determination to a field service engineer.

The alert may comprise information regarding how to identify whether a carrier for the cathode of the electron gun is loose or whether there are loose connections on the gun body or issues with the gun isolation transformer.

The alert may also comprise how to fix these issues. Outputting the determination may also comprise issuing a communication, alert, or otherwise contacting the owner of the radiotherapy device in order to inform them of the issue and to schedule maintenance of the radiotherapy device.

In an example, once the criteria described herein and set out in the flowchart of FIGS. 9a and 9b have been met, a report is generated and an alert is raised. This alert is then sent to the relevant service team and they will plan maintenance of the radiotherapy device.

In a preferred embodiment, the device controller 240 receives signals from the voltage sensor and the gantry rotation sensor and transmits them to the remote controller 260. The central controller 270 receives the signals and then derives the voltage values and gantry angle values. Voltage values may be derived by calculating the average voltage values from the signals over a time period, the sensor being determined to remain at the same gantry angle for this period of time. Each average voltage value and corresponding gantry angle value are stored on the central controller memory 270. Processing of the voltage values and the gantry angle values takes place when the remote controller 260 accesses the central memory 275 via the network 250. However, at least some of the steps, and in some examples all of the steps, displayed in FIGS. 9a and 9b may be performed on the device controller 240. It will be appreciated that any combination of the device controller 240 central controller 270 and remote controller 260 may be used to perform the disclosed methods.

Reference is now made to the flowchart of FIG. 10. The flowchart shows how notification of a fault in step 910 is generated. The process identifies shorts or partial shorts in the electron gun which can be indicative of the electron gun, or components of the electron gun, coming lose.

At step 1010, a current value is received. The current value is derived from signals from the current sensor. The current value may be directly indicative of the signals from the current sensor at any particular instance and may vary as signals from the current sensor vary. To this end, the current value may be updated continuously.

At step 1020, the current value is processed. In a preferred embodiment, the processing of the current value comprises determining whether the current value meets at least a third threshold criterion. Optionally, this comprises determining that the current value has fallen below a threshold current value, for example below 1 A.

At step 1030, a voltage value is received. The voltage value is derived from signals from the voltage sensor. The voltage value may be directly indicative of the signals from the voltage sensor at any particular instance and may vary as signals from the voltage sensor vary. To this end, the voltage value may be updated continuously.

At step 1040, the voltage value is processed. In a preferred embodiment, the processing of the voltage value comprises determining whether the voltage value meets at least a fourth threshold criterion. Optionally, this comprises determining that the voltage value is greater than a second threshold voltage value, for example above 35 A.

At step 1050, a notification indicative of a fault in the radiotherapy device is generated when one or both of the third and fourth threshold criteria are met. For example, if the current value has fallen below the threshold current value and/or the voltage value is greater than the second threshold voltage value, a notification indicative of a fault in the radiotherapy device may be generated. Either or both of the third and fourth threshold criteria being met may be indicative of the electron gun, or components of the electron gun, coming loose and causing partial shorts.

It will be appreciated that while a specific order of steps is set out in FIGS. 5, 8a, 8b, 9a, 9b and 10, these steps may be performed in a different order.

Examples of the present disclosure are set out in the following numbered clauses.

1. A method of determining whether maintenance of a radiotherapy device should be scheduled, the radiotherapy device comprising a linear accelerator and being configured to provide therapeutic radiation to a patient, the radiotherapy device comprising:
a current sensor, the current sensor being configured to provide signals indicative of current supplied to an electron gun of the radiotherapy device; and a vacuum tube comprising:
the electron gun; and
a waveguide configured to accelerate electrons emitted by the electron gun toward a target to produce said radiation;
the method comprising:
receiving a current value derived from signals provided by the current sensor;
processing the current value to determine whether the current value meets at least a first threshold criterion;
determining whether a total amount of time the electron gun has been in a radiation mode meets at least a second threshold criterion; and
if the first threshold criterion and the second threshold criterion are met, determining whether maintenance of the radiotherapy device should be scheduled.

2. The method of clause 1, wherein determining whether the current value meets the first threshold criterion comprises determining that the current value has fallen below a threshold current value, optionally, wherein the threshold current value is 7.35 A.

3. The method of any preceding clause, wherein the current value is an average of signals received from the current sensor over an averaging time period, optionally, wherein the averaging time period is a day.

4. The method of any preceding clause, wherein determining whether the total amount of time the electron gun has been in a radiation mode meets the second threshold criterion comprises determining that the total amount of time the electron gun has been in a radiation mode is less than a threshold time period, optionally, wherein the time period is 600 hours.

5. The method of any preceding clause, further comprising outputting the determination of whether maintenance of the radiotherapy device should be scheduled.

6. The method of clause 5, wherein outputting the determination comprises at least one of displaying an indication of the determination on a display screen; issuing an alert detailing the determination to a field service engineer; and/or automatically issuing a notification to the owner of the radiotherapy device to schedule maintenance of the radiotherapy device.

7. The method of any preceding clause, the radiotherapy device further comprising a pressure sensor, the pressure sensor being configured to provide signals indicative of a pressure inside the vacuum tube,
the method further comprising:
receiving a pressure value derived from signals from the pressure sensor, the pressure value being indicative of pressure inside the vacuum tube;
processing the pressure value to determine whether the pressure value meets at least a third threshold criterion; and
if the third threshold criterion is met, determining whether maintenance of the radiotherapy device should be scheduled.

8. The method of clause 7, wherein determining whether the pressure value meets the third threshold criterion comprises determining that the pressure value has fallen below a threshold pressure value.

9. The method of clause 7 or clause 8, wherein the pressure value is an average of signals received from the pressure sensor over an averaging time period, optionally, wherein the averaging time period is seven days.

10. A computer-readable medium comprising computer-executable instructions which, when executed by a processor, cause the processor to perform the method of any preceding clause.

11. A system comprising a remote controller communicatively coupled to a central controller via a network, the central controller configured to receive data from a radiotherapy device, the radiotherapy device comprising a linear accelerator and being configured to provide therapeutic radiation to a patient, and the radiotherapy device comprising:
a current sensor, the current sensor being configured to provide signals indicative of current supplied to an electron gun of the radiotherapy device; and
a vacuum tube comprising:
the electron gun; and
a waveguide configured to accelerate electrons emitted by the electron gun toward a target to produce said radiation,
wherein the remote controller is coupled to a computer-readable medium comprising computer-executable instructions which, when executed by the remote controller, cause the remote controller to:
request, from the central controller, a current value; and
perform the method of any of clauses 1 to 6.

12. The system of clause 11, wherein the radiotherapy device further comprises a pressure sensor, the pressure sensor being configured to provide signals indicative of a vacuum quality of the vacuum tube,
wherein the computer-executable instructions, when executed by the remote controller, further cause the remote controller to perform the method of either of clauses 1 to 9.

13. A method of determining the nature of a fault in a radiotherapy device, the radiotherapy device comprising a linear accelerator and being configured to provide therapeutic radiation to a patient, the radiotherapy device comprising:
a gantry configured to rotate the vacuum tube around a patient such that radiation can be directed toward the patient from multiple angles and/or directions around the patient;
a voltage sensor, configured to provide signals indicative of voltage applied to an electron gun of the radiotherapy device; and
a vacuum tube comprising:
the electron gun; and
a waveguide configured to accelerate electrons emitted by the electron gun toward a target to produce said radiation,
the method comprising:
receiving voltage values derived from signals provided by the voltage sensor during a rotation of the gantry;
processing the voltage values, wherein processing the voltage values comprises determining whether the voltage values meet at least one first threshold criterion; and
based on the processing of the voltage values, determining whether the nature of the fault is associated with the electron gun.

14. The method of clause 13, wherein determining whether the voltage values meet the at least one first threshold criterion comprises determining whether the voltage values vary by at least a threshold amount during the rotation of the gantry.

15. The method of clause 14, wherein the threshold amount is 0.2 volts.

16. The method of any preceding clause, wherein processing the voltage values further comprises determining whether the electron gun is in a standby mode during the rotation of the gantry by determining whether the voltage values meet at least one second threshold criterion.

17. The method of clause 16, wherein determining whether the voltage values meet at least one second threshold criterion comprises determining whether the voltage values are less than a first threshold voltage value.

18. The method of clause 17, wherein the first threshold voltage is 15 volts.

19. The method of any preceding clause, the radiotherapy device further comprising a gantry rotation sensor configured to provide a signal indicative of the degree to which the gantry has been rotated,
the method further comprising:
receiving a gantry angle value derived from signals provided by the gantry rotation sensor for each of the received voltage values, wherein each gantry angle value is indicative of the degree to which the gantry is rotated when each voltage value is generated; and
processing the gantry angle values to determine whether the rotation of the gantry has met at least one fifth threshold criterion.

20 The method of clause 19, wherein determine whether the rotation of the gantry has met a fifth threshold criterion comprises determining whether the rotation of the gantry exceeds a threshold degree of rotation, optionally, wherein the degree of rotation is 90 degrees.

21. The method of any preceding clause, further comprising outputting the determination of whether the nature of the fault is associated with the electron gun.

22. The method of clause 21, wherein outputting the determination comprises at least one of displaying an indication of the determination on a display screen; issuing an alert detailing the determination to a field service engineer; and/or automatically issuing a notification to the owner of the radiotherapy device to schedule a repair or replacement.

23. The method of any preceding clause, further comprising receiving or generating a notification of a fault in the radiotherapy device.

24. The method of any of clauses 13 to 22, the radiotherapy device further comprising a current sensor, the current sensor being configured to provide signals indicative of current supplied to the electron gun,
the method further comprising:
receiving a current value derived from signals provided by the current sensor;
processing the current value, wherein processing the current value comprises determining whether the current value meets at least a third threshold criterion;
receiving a second voltage value derived from signals provided by the sensor; and
processing the second voltage value, wherein processing the second voltage value comprises determining whether the second voltage value meets at least a fourth threshold criterion;
based on processing the current value and the second voltage value, generating a notification of a fault in the radiotherapy device.

25. The method of clause 24, wherein determining whether the current value meets at least the third threshold criterion comprises determining whether the current value is less than a threshold current, optionally wherein the threshold current is 1 A.

26. The method of clause 24 or clause 25, wherein determining whether the second voltage value meets at least the fourth threshold criterion comprises determining whether the second voltage is greater than a second threshold voltage, optionally wherein the second voltage threshold is 35V.

27. A system comprising a remote controller communicatively coupled to a central controller via a network, the central controller configured to receive data from a radiotherapy device, the radiotherapy device comprising a linear accelerator and being configured to provide therapeutic radiation to a patient, and the radiotherapy device comprising:
a gantry configured to rotate the vacuum tube around a patient such that radiation can be directed toward the patient from multiple angles and/or directions around the patient;
a voltage sensor, configured to provide signals indicative of a voltage of an electron gun of the radiotherapy device; and
a vacuum tube comprising:
the electron gun; and
a waveguide configured to accelerate electrons emitted by the electron gun toward a target to produce said radiation,
wherein the remote controller is coupled to a computer-readable medium comprising computer-executable instructions which, when executed by the remote controller, cause the remote controller to:
request and receive, from the central controller, voltage values derived from signals provided by the voltage sensor during a rotation of the gantry; and
perform the method of any of clauses 13 to 23.

28. The system of clause 27, wherein the radiotherapy device further comprises a current sensor, the current sensor being configured to provide signals indicative of current supplied to the electron gun,
wherein the computer-executable instructions, when executed by the remote controller, further cause the remote controller to perform the method of any of clauses 13 to 18 and 21 to 26.

29. The system of clause 27 or clause 28, wherein the radiotherapy device further comprises a gantry rotation sensor configured to provide a signal indicative of the degree to which the gantry has been rotated,
wherein the computer-executable instructions, when executed by the remote controller, further cause the remote controller to perform the method of any of clauses 13 to 26.

30. A method of determining the nature of a fault in a radiotherapy device, the radiotherapy device comprising a linear accelerator and being configured to provide therapeutic radiation to a patient, the radiotherapy device comprising:
a current sensor, configured to provide signals indicative of current applied to an electron gun of the radiotherapy device;
a voltage sensor, configured to provide signals indicative of voltage applied to the electron gun; and
a vacuum tube comprising:
the electron gun;
a waveguide configured to accelerate electrons emitted by the electron gun toward a target to produce said radiation,
the method comprising:
receiving a current value derived from signals provided by the current sensor;

processing the current value, wherein processing the current value comprises determining whether the current value meets at least a first threshold criterion;
receiving a voltage value derived from signals provided by the sensor; and
processing the voltage value, wherein processing the voltage value comprises determining whether the voltage value meets at least a second threshold criterion;
based on processing the current value and the voltage value, generating a notification of a fault in the radiotherapy device.

31. The method of clause 30, wherein determining whether the current value meets at least the first threshold criterion comprises determining whether the current value is less than a current threshold, optionally wherein the current threshold is 1 A.

32. The method of clause 30 or clause 31, wherein determining whether the voltage value meets at least the second threshold criterion comprises determining whether the voltage is greater than a threshold voltage value, optionally wherein the threshold voltage value is 35V.

33. A system comprising a remote controller communicatively coupled to a central controller via a network, the central controller configured to receive data from a radiotherapy device, the radiotherapy device comprising a linear accelerator and being configured to provide therapeutic radiation to a patient, and the radiotherapy device comprising:
a current sensor, configured to provide signals indicative of current applied to an electron gun of the radiotherapy device;
a voltage sensor, configured to provide signals indicative of a voltage of the electron gun; and
a vacuum tube comprising:
the electron gun;
a waveguide configured to accelerate electrons emitted by the electron gun toward a target to produce said radiation,
wherein the remote controller is coupled to a computer-readable medium comprising computer-executable instructions which, when executed by the remote controller, cause the remote controller to:
request and receive, from the central controller, voltage values derived from signals provided by the voltage sensor during a rotation of the gantry; and
perform the method of any of clauses 30 to 32.

34. A computer-readable medium comprising computer-executable instructions which, when executed by a processor, cause the processor to perform the method of any of clauses.

All the methods of the present disclosure may be described as computer-implemented methods. Repair of the electron gun, as described herein, may comprise replacing the cathode filament. The present techniques therefore describe a cost-effective, efficient and predictive method of preventing a fault. It has to date proved impossible to determine the condition of in-service electron guns in order to predict when maintenance should be performed. The present approach provides cost and time savings over the prior methods because servicing and maintenance in the form of repair and replacement of the electron gun, or other components of radiotherapy devices, is only performed when needed, and downtime of the device is reduced due to reducing or eliminating entirely the number of safety interrupts usually associated with a degrading cathode filament, and also by eliminating time spent diagnosing the problem before repair is effected.

The above implementations have been described by way of example only, and the described implementations and arrangements are to be considered in all respects only as illustrative and not restrictive. It will be appreciated that variations of the described implementations and arrangements may be made without departing from the scope of the invention.

The invention claimed is:

1. A system for determining whether repair or replacement of an electron gun of a radiotherapy device configured to provide therapeutic radiation to a patient should be scheduled, the system comprising:
the radiotherapy device, the radiotherapy device comprising:
a linear accelerator;
a vacuum tube comprising:
the electron gun;
a waveguide configured to accelerate electrons emitted by the electron gun toward a target to produce said radiation; and
a current sensor, configured to provide a signal indicative of current supplied to the electron gun;
a processor configured to:
receive current values derived from the signal provided by the current sensor;
process the current values, wherein to process the current values comprises:
when the current values have fallen below a first threshold current value, determine whether the current values have changed by a first threshold amount in a particular time period;
when the current values have fallen below a second threshold current value, determine whether the current values have changed by a second threshold amount in the particular time period, wherein the first threshold current value is lower than the second threshold current value, and wherein the first threshold amount is smaller than the second threshold amount;
receive a voltage value derived from a signal provided by a voltage sensor during a rotation of a gantry;
process the voltage value, wherein to process the voltage value comprises a determination of whether the electron gun is in a standby mode during the rotation of the gantry, wherein the determination of whether the electron gun is in standby mode is made by a determination of whether the voltage value meets at least one voltage threshold criterion; and
based on the processed current values, determine that repair or replacement of the electron gun should be scheduled when either: i) the current values have fallen below the first threshold current value and have changed by at least the first threshold amount in the particular time period, or ii) the current values have fallen below the second threshold current value and the current values have changed by at least the second threshold amount in the particular time period.

2. The system of claim 1, wherein the current values include an average of multiple signals received from the current sensor over an averaging time period, wherein the averaging time period is one day.

3. The system of claim 2, wherein the processor is further configured to:
derive the current values based on the multiple signals received from the current sensor, wherein the deriving comprises:
calculation of an average of the multiple signals received from the current sensor over the averaging time period.

4. The system of claim 1, wherein the processor is further configured to:
output the determination of whether repair or replacement of the electron gun should be scheduled, wherein to output the determination comprises at least one of: i) display an indication of the determination on a display screen, ii) issue an alert detailing the determination to a field service engineer, or iii) automatically issue a notification to an owner of the radiotherapy device to schedule the repair or replacement.

5. The system of claim 1, further comprising:
in response to a determination that the current values have fallen below the second threshold current value and the current values have changed by at least the second threshold amount in the particular time period, outputting an indication that the electron gun should be repaired or replaced as a high priority.

6. A method of determining whether repair or replacement of an electron gun of a radiotherapy device should be scheduled, the radiotherapy device comprising a linear accelerator and being configured to provide therapeutic radiation to a patient, the radiotherapy device comprising:
a vacuum tube comprising the electron gun, a waveguide configured to accelerate electrons emitted by the electron gun toward a target to produce the therapeutic radiation; and a current sensor, the current sensor being configured to provide a signal indicative of current supplied to the electron gun;
the method comprising:
receiving a voltage value derived from a signal provided by a voltage sensor during rotation of a gantry:
processing the voltage value, wherein processing the voltage value comprises a determination of whether the electron gun is in a standby mode during the rotation of the gantry, and wherein the determination of whether the electron gun is in standby mode is made by a determination of whether the voltage value meets at least one voltage threshold criterion;
receiving current values derived from the signal provided by the current sensor;
processing the current values, wherein processing the current values comprises:
when the current values have fallen below a first threshold current value, determining whether the current values have changed by a first threshold amount in a particular time period; and
when the current values have fallen below a second threshold current value, determining whether the current values have changed by a second threshold amount in the particular time period, wherein the first threshold current value is lower than the second threshold current value, and wherein the first threshold amount is smaller than the second threshold amount; and
based on the processed current values, determining that repair or replacement of the electron gun should be scheduled when either: I) the current values have fallen below the first threshold current value and have changed by at least the first threshold amount in the particular time period, or ii) the current values have fallen below the second threshold current value and the current values have changed by at least the second threshold amount in the particular time period.

7. A system for determining a nature of a fault in a radiotherapy device configured to provide therapeutic radiation to a patient, the system comprising:
the radiotherapy device, the radiotherapy device comprising:
a linear accelerator;
a gantry configured to rotate a vacuum tube around a patient such that radiation is directed toward the patient from multiple angles or directions around the patient, the vacuum tube comprising:
an electron gun;
a waveguide configured to accelerate electrons emitted by the electron gun toward a target to produce said radiation;
a voltage sensor, configured to provide a signal indicative of a voltage applied to the electron gun;
a current sensor configured to provide a signal indicative of current supplied to the electron gun; and
a processor configured to:
receive a voltage value derived from signal provided by the voltage sensor during a rotation of the gantry;
process the voltage value, wherein to process the voltage value comprises a determination of whether the voltage value meets at least one first threshold criterion, wherein processing the voltage value further comprises a determination of whether the electron gun is in a standby mode during the rotation of the gantry, and wherein the determination of whether the electron gun is in standby mode is made by a determination of whether the voltage value meets at least one second threshold criterion; and
based on the processing of the voltage value, determine whether a fault is present in the radiotherapy device, and in response to a determination that a fault is present in the radiotherapy device, determine whether the nature of the fault is associated with the electron gun;
receive current values derived from the signal provided by the current sensor;
process the current values, wherein the process the current values includes:
when the current values have fallen below a first current threshold value, determine whether the current values have changed by a first current threshold amount in a particular time period; and
when the current values have fallen below a second current threshold value, determine whether the current values have changed by a second current threshold amount in the particular time period, wherein the first current threshold value is lower than the second current threshold value, and wherein the first current threshold amount is smaller than the second current threshold amount;
receive a second voltage value derived from a second signal provided by the voltage sensor;
process the second voltage value, wherein the process the second voltage value comprises a determination of whether the second voltage value meets at least a fourth threshold criterion; and
based on the processed current values and the processed second voltage value, generate a notification of a fault in the radiotherapy device, wherein the notification includes that the electron gun should be repaired or replaced when either: i) the current values have fallen below the first current threshold value and have changed by at least the first current threshold amount in the particular time period, or ii) the current values have fallen below the second current threshold value and the current values have changed at least by the second current threshold amount in the particular time period.

8. The system of claim 7, wherein to determine whether the voltage value meets the at least one first threshold criterion comprises a determination of whether the voltage value varies by at least a threshold amount during the rotation of the gantry.

9. The system of claim 7, wherein determining whether the voltage value meets at least one second threshold criterion comprises a determination of whether the voltage values are less than a first threshold voltage value.

10. The system of claim 7, the radiotherapy device further comprising a gantry rotation sensor configured to provide a signal indicative of a degree to which the gantry has been rotated, and wherein the processor is further configured to:
receive a gantry angle value derived from a signal provided by the gantry rotation sensor for the received voltage value, wherein the gantry angle value is indicative of the degree to which the gantry is rotated when the voltage value is generated; and
process the gantry angle value to determine whether the rotation of the gantry has met at least one fifth threshold criterion.

11. The system of claim 7, wherein the process is further to:
output the determination of whether the nature of the fault is associated with the electron gun, wherein to output the determination of whether the nature of the fault is associated with the electron gun comprises at least one of: display an indication of the determination on a display screen, issue an alert detailing the determination to a field service engineer, or automatically issue a notification to an owner of the radiotherapy device to schedule a repair or replacement.

12. The system of claim 7, further comprising:
determining whether the current value meets at least a third threshold criterion, wherein determining whether the current value meets at least the third threshold criterion comprises determining whether the current value is less than a threshold current.

13. The system of claim 7, wherein to determine whether the second voltage value meets at least the fourth threshold criterion comprises a determination of whether the second voltage value is greater than a second threshold voltage.

* * * * *